United States Patent [19]

Vehar et al.

[11] Patent Number: 5,714,372
[45] Date of Patent: Feb. 3, 1998

[54] TISSUE PLASMINOGEN ACTIVATOR VARIANTS

[75] Inventors: Gordon A. Vehar, San Carlos; Herbert L. Heyneker, Hillsborough, both of Calif.

[73] Assignee: Genentech, Inc., South San Francisco, Calif.

[21] Appl. No.: 306,928

[22] Filed: Sep. 15, 1994

Related U.S. Application Data

[63] Continuation of Ser. No. 101,276, Aug. 2, 1993, abandoned, which is a continuation of Ser. No. 808,366, Dec. 16, 1991, abandoned, which is a continuation-in-part of Ser. No. 741,120, Aug. 5, 1991, Pat. No. 5,147,643, which is a division of Ser. No. 522,480, May 11, 1990, Pat. No. 5,073,494, which is a continuation of Ser. No. 186,494, Apr. 26, 1988, abandoned, which is a continuation of Ser. No. 71,506, Jul. 9, 1987, abandoned, which is a continuation-in-part of Ser. No. 846,697, Apr. 1, 1986, abandoned, which is a continuation-in-part of Ser. No. 725,468, Apr. 22, 1985, abandoned.

[51] Int. Cl.$^6$ .............................. C12N 9/50; C12N 9/64; C12N 15/55; C12N 5/10
[52] U.S. Cl. .............. 435/226; 435/212; 424/94.64; 536/23.2
[58] Field of Search ................... 435/69.1, 212, 435/226, 172.3, 240.1, 240.2, 252.3, 254.11; 536/23.2; 424/94.64

[56] References Cited

U.S. PATENT DOCUMENTS

| | | |
|---|---|---|
| 4,753,879 | 6/1988 | Rosa et al. ............. 435/172.3 |
| 4,935,237 | 6/1990 | Higgins et al. ............ 424/94.64 |
| 5,094,953 | 3/1992 | Anderson et al. ............ 435/226 |

FOREIGN PATENT DOCUMENTS

| | | |
|---|---|---|
| 201153 | 12/1986 | European Pat. Off. |
| 233103 | 8/1987 | European Pat. Off. |
| 241209 | 10/1987 | European Pat. Off. |
| 292009 | 11/1988 | European Pat. Off. |
| 293934 | 12/1988 | European Pat. Off. |
| 293936 | 12/1988 | European Pat. Off. |
| 8810119 | 12/1988 | WIPO . |

OTHER PUBLICATIONS

Pennica, D. et al., Nature, vol. 301, pp. 214–221, 1983.

Tate, K. et al., Biochemistry, vol. 26, pp. 338–343, Jan. 1987.

*Primary Examiner*—Dian C. Jacobson
*Attorney, Agent, or Firm*—Walter H. Dreger; Robin M. Silva

[57] ABSTRACT

Biologically active mutant tissue plasminogen activators are disclosed wherein site directed mutagenesis, for example, of a two-chain activation site renders said mutants resistant to conversion to the two-chain form. In addition, mutant tissue plasminogen activators are disclosed which have amino acid substitutions or deletions in the region of positions 274–277, which may or may not be resistant to conversion to the two-chain form, but show enhanced fibrin specificity relative to wild-type tissue plasminogen activator.

7 Claims, 21 Drawing Sheets

```
GTTCTGAGCACAGGGCTGGAGAGAAAACCTCTGCGAGGAAAGGGAAGGAGCAAGCCGTGA
                                 -35                      -30
                                 met asp ala met lys arg gly leu
         ATTTAAGGGACGCTGTGAAGCAATC ATG GAT GCA ATG AAG AGA GGG CTC
                                 -20
cys cys val leu leu leu cys gly ala val phe val ser pro ser
TGC TGT GTG CTG CTG CTG TGT GGA GCA GTC TTC GTT TCG CCC AGC
        -10                                              1
gln glu ile his ala arg phe arg arg gly ala arg SER TYR GLN
CAG GAA ATC CAT GCC CGA TTC AGA AGA GGA GCC AGA TCT TAC CAA
                            10
VAL ILE CYS ARG ASP GLU LYS THR GLN MET ILE TYR GLN GLN HIS
GTG ATC TGC AGA GAT GAA AAA ACG CAG ATG ATA TAC CAG CAA CAT
    20                                      30
GLN SER TRP LEU ARG PRO VAL LEU ARG SER ASN ARG VAL GLU TYR
CAG TCA TGG CTG CGC CCT GTG CTC AGA AGC AAC CGG GTG GAA TAT
                        40
CYS TRP CYS ASN SER GLY ARG ALA GLN CYS HIS SER VAL PRO VAL
TGC TGG TGC AAC AGT GGC AGG GCA CAG TGC CAC TCA GTG CCT GTC
 50                                          60
LYS SER CYS SER GLU PRO ARG CYS PHE ASN GLY GLY THR CYS GLN
AAA AGT TGC AGC GAG CCA AGG TGT TTC AAC GGG GGC ACC TGC CAG
                    70
GLN ALA LEU TYR PHE SER ASP PHE VAL CYS GLN CYS PRO GLU GLY
CAG GCC CTG TAC TTC TCA GAT TTC GTG TGC CAG TGC CCC GAA GGA
 80                                          90
PHE ALA GLY LYS CYS CYS GLU ILE ASP THR ARG ALA THR CYS TYR
TTT GCT GGG AAG TGC TGT GAA ATA GAT ACC AGG GCC ACG TGC TAC
                   100
GLU ASP GLN GLY ILE SER TYR ARG GLY THR TRP SER THR ALA GLU
GAG GAC CAG GGC ATC AGC TAC AGG GGC ACG TGG AGC ACA GCG GAG
 110                                         120
SER GLY ALA GLU CYS THR ASN TRP ASN SER SER ALA LEU ALA GLN
AGT GGC GCC GAG TGC ACC AAC TGG AAC AGC AGC GCG TTG GCC CAG
                   130
LYS PRO TYR SER GLY ARG ARG PRO ASP ALA ILE ARG LEU GLY LEU
AAG CCC TAC AGC GGG CGG AGG CCA GAC GCC ATC AGG CTG GGC CTG
 140                                         150
GLY ASN HIS ASN TYR CYS ARG ASN PRO ASP ARG ASP SER LYS PRO
GGG AAC CAC AAC TAC TGC AGA AAC CCA GAT CGA GAC TCA AAG CCC
                   160
TRP CYS TYR VAL PHE LYS ALA GLY LYS TYR SER SER GLU PHE CYS
TGG TGC TAC GTC TTT AAG GCG GGG AAG TAC AGC TCA GAG TTC TGC
 170                                         180
SER THR PRO ALA CYS SER GLU GLY ASN SER ASP CYS TYR PHE GLY
AGC ACC CCT GCC TGC TCT GAG GGA AAC AGT GAC TGC TAC TTT GGG
```

Fig. 2A

```
                              190
ASN GLY SER ALA TYR ARG GLY THR HIS SER LEU THR GLU SER GLY
AAT GGG TCA GCC TAC CGT GGC ACG CAC AGC CTC ACC GAG TCG GGT
    200                                         210
ALA SER CYS LEU PRO TRP ASN SER MET ILE LEU ILE GLY LYS VAL
GCC TCC TGC CTC CCG TGG AAT TCC ATG ATC CTG ATA GGC AAG GTT
                              220
TYR THR ALA GLN ASN PRO SER ALA GLN ALA LEU GLY LEU GLY LYS
TAC ACA GCA CAG AAC CCC AGT GCC CAG GCA CTG GGC CTG GGC AAA
    230                                         240
HIS ASN TYR CYS ARG ASN PRO ASP GLY ASP ALA LYS PRO TRP CYS
CAT AAT TAC TGC CGG AAT CCT GAT GGG GAT GCC AAG CCC TGG TGC
                              250
HIS VAL LEU LYS ASN ARG ARG LEU THR TRP GLU TYR CYS ASP VAL
CAC GTG CTG AAG AAC CGC AGG CTG ACG TGG GAG TAC TGT GAT GTG
    260                                         270
PRO SER CYS SER THR CYS GLY LEU ARG GLN TYR SER GLN PRO GLN
CCC TCC TGC TCC ACC TGC GGC CTG AGA CAG TAC AGC CAG CCT CAG
                              280
PHE ARG ILE LYS GLY GLY LEU PHE ALA ASP ILE ALA SER HIS PRO
TTT CGC ATC AAA GGA GGG CTC TTC GCC GAC ATC GCC TCC CAC CCC
    290                                         300
TRP GLN ALA ALA ILE PHE ALA LYS HIS ARG ARG SER PRO GLY GLU
TGG CAG GCT GCC ATC TTT GCC AAG CAC AGG AGG TCG CCC GGA GAG
                              310
ARG PHE LEU CYS GLY GLY ILE LEU ILE SER SER CYS TRP ILE LEU
CGG TTC CTG TGC GGG GGC ATA CTC ATC AGC TCC TGC TGG ATT CTC
    320                                         330
SER ALA ALA HIS CYS PHE GLN GLU ARG PHE PRO PRO HIS HIS LEU
TCT GCC GCC CAC TGC TTC CAG GAG AGG TTT CCG CCC CAC CAC CTG
                              340
THR VAL ILE LEU GLY ARG THR TYR ARG VAL VAL PRO GLY GLU GLU
ACG GTG ATC TTG GGC AGA ACA TAC CGG GTG GTC CCT GGC GAG GAG
    350                                         360
GLU GLN LYS PHE GLU VAL GLU LYS TYR ILE VAL HIS LYS GLU PHE
GAG CAG AAA TTT GAA GTC GAA AAA TAC ATT GTC CAT AAG GAA TTC
                              370
ASP ASP ASP THR TYR ASP ASN ASP ILE ALA LEU LEU GLN LEU LYS
GAT GAT GAC ACT TAC GAC AAT GAC ATT GCG CTG CTG CAG CTG AAA
    380                                         390
SER ASP SER SER ARG CYS ALA GLN GLU SER SER VAL VAL ARG THR
TCG GAT TCG TCC CGC TGT GCC CAG GAG AGC AGC GTG GTC CGC ACT
                              400
VAL CYS LEU PRO PRO ALA ASP LEU GLN LEU PRO ASP TRP THR GLU
GTG TGC CTT CCC CCG GCG GAC CTG CAG CTG CCG GAC TGG ACG GAG
    410                                         420
CYS GLU LEU SER GLY TYR GLY LYS HIS GLU ALA LEU SER PRO PHE
TGT GAG CTC TCC GGC TAC GGC AAG CAT GAG GCC TTG TCT CCT TTC
```

*Fig. 2B*

```
                           430
TYR SER GLU ARG LEU LYS GLU ALA HIS VAL ARG LEU TYR PRO SER
TAT TCG GAG CGG CTG AAG GAG GCT CAT GTC AGA CTG TAC CCA TCC
    440                                     450
SER ARG CYS THR SER GLN HIS LEU LEU ASN ARG THR VAL THR ASP
AGC CGC TGC ACA TCA CAA CAT TTA CTT AAC AGA ACA GTC ACC GAC
                       460
ASN MET LEU CYS ALA GLY ASP THR ARG SER GLY GLY PRO GLN ALA
AAC ATG CTG TGT GCT GGA GAC ACT CGG AGC GGC GGG CCC CAG GCA
    470                                 480
ASN LEU HIS ASP ALA CYS GLN GLY ASP SER GLY GLY PRO LEU VAL
AAC TTG CAC GAC GCC TGC CAG GGC GAT TCG GGA GGC CCC CTG GTG
                   490
CYS LEU ASN ASP GLY ARG MET THR LEU VAL GLY ILE ILE SER TRP
TGT CTG AAC GAT GGC CGC ATG ACT TTG GTG GGC ATC ATC AGC TGG
    500                                 510
GLY LEU GLY CYS GLY GLN LYS ASP VAL PRO GLY VAL TYR THR LYS
GGC CTG GGC TGT GGA CAG AAG GAT GTC CCG GGT GTG TAC ACC AAG
                       520                             527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA
CCAGGAACACCCGACTCCTCAAAAGCAAATGAGATCCGCCTCTTCTTCTTCAGAAGACA
CTGCAAAGGCGCAGTGCTTCTCTACAGACTTCTCCAGACCCACCACACCGCAGAAGCGGG
ACGAGACCCTACAGGAGAGGGAAGAGTGCATTTTCCCAGATACTTCCCATTTTGGAAGT
TTTCAGGACTTGGTCTGATTTCAGGATACTCTGTCAGATGGGAAGACATGAATGCACACT
AGCCTCTCCAGGAATGCCTCCTCCCTGGGCAGAAAGTGGCCATGCCACCCTGTTTTCAGCTA
AAGCCCAACCTCCTGACCTGTCACCGTGAGCAGCTTTGGAAACAGGACCACAAAAATGAA
AGCATGTCTCAATAGTAAAAGATAACAAGATCTTTCAGGAAAGACGGATTGCATTAGAA
ATAGACAGTATATTTATAGTCACAAGAGCCCAGCAGGGCCTCAAAGTTGGGGCAGGCTGGC
TGGCCCGTCATGTTCCTCAAAAGCACCCTTGACGTCAAGTCTCCTTCCCCTTTCCCCACT
CCCTGGCTCTCAGAAGGTATTCCTTTTGTGTACAGTGTGTAAAGTGTAAATCCTTTTTCT
TTATAAACTTTAGAGTAGCATGAGAGAATTGTATCATTTGAACAACTAGGCTTCAGCATA
TTTATAGCAATCCATGTTAGTTTTTACTTTCTGTTGCCACAACCCTGTTTTATACTGTA
CTTAATAAATTCAGATATATTTTTCACAGTTTTTCCAAAAAAAAAAAAAA
```

*Fig. 2C*

TISSUE PLASMINOGEN ACTIVATOR VARIANTS

This is a continuation of application Ser. No. 08/101,276 filed 2 Aug. 1993 now abandoned, which application is a continuation of U.S. Ser. No. 07/808,366, filed 16 Dec. 1991, now abandoned, which is a continuation-in-part of U.S. Ser. No. 07/741,120, filed 5 Aug. 1991, now U.S. Pat. No. 5,147,643, which is a divisional application of U.S. Ser. No. 07/522,480, filed 11 May 1990, now U.S. Pat. No. 5,073,494, which is a continuation application of U.S. Ser. No. 07/186,494, filed 26 Apr. 1988, abandoned, which is a continuation application of U.S. Ser. No. 07/071,506, filed 9 Jul. 1987, abandoned, which is a continuation-in-part application of U.S. Ser. No. 06/846,697, filed 1 Apr. 1986, abandoned, which is a continuation-in-part application of U.S. Ser. No. 06/725,468, filed 22 Apr. 1985, abandoned.

This application is related to Application Ser. No. 07/808537, filed on even date herewith.

FIELD OF THE INVENTION

The present invention is directed to particular novel variants of tissue plasminogen activator (t-PA). These variants, although embraced generically by earlier disclosure, as noted infra, are novel, specific derivatives which exhibit activities which defied prediction from the prior research of others on the basic tissue plasminogen activator molecule or the model serine proteases trypsin and chymotrypsin.

As the preferred embodiment herein contemplates the preparation of such variants via recombinant DNA technology, the present invention likewise encompasses the associated compounds and means involved in such technology, namely, DNA isolates encoding such variants, expression vectors, transfected host cells and processes for making and using each of them. The novel variants hereof have unexpectedly enhanced fibrin specificity.

BACKGROUND OF THE INVENTION

Plasminogen activators are enzymes that activate the zymogen plasminogen to generate the serine proteinase plasmin (by cleavage at Arg561-Val1562) that degrades various proteins, including fibrin. Among the plasminogen activators studied are streptokinase, a bacterial protein, urokinase, an enzyme synthesized in the kidney and elsewhere and originally extracted from urine, and tissue plasminogen activator (t-PA), an enzyme produced by the cells lining blood vessel walls.

The mechanism of action of each of these plasminogen activators differs: Streptokinase forms a complex with plasminogen or plasmin, generating plasminogen-activating activity, urokinase cleaves plasminogen directly, and t-PA, fibrin, and plasminogen all interact to yield maximum activity.

t-PA has been identified and described as a particularly important and potent new biological pharmaceutical agent that has shown extraordinary results in the treatment of vascular diseases, such as myocardial infarction, due in part to its fibrin specificity and potent ability to dissolve blood clots in vivo.

Tissue plasminogen activator was first identified as a substantially pure isolate from a natural source, and tested for requisite plasminogen activator activity by Collen, et al., European Patent Application Publication No. 041766, published 16 Dec. 1981, based upon a first filing of 11 Jun. 1980. See also U.S. Pat. No. 4,752,603, issued 21 Jun. 1988 and Rijken, et al., *J. Biol. Chem.* 256, 7035 (1981).

Subsequently, researchers in Assignee's laboratories produced large quantities of tissue plasminogen activator, fully characterized by underlying DNA and deduced amino acid sequences, essentially free of proteins with which it is ordinarily associated, in a distinct milieu, via recombinant DNA technology. This work has been recorded in the scientific literature and in European Patent Application Publication No. 093619 published 9 Nov. 1983, based upon a first filing on 5 May 1982. See also U.S. Pat. No. 4,766,075, issued 23 Aug. 1988 and Pennica, et al., *Nature* 301, 214 (1983). The above patent application (EPO Publication No. 093619) contemplates the production of various human plasminogen activator derivatives, variously modified by amino acid substitutions, deletions, additions, or replacements prepared, for example, by site directed mutagenesis of the underlying DNA.

As disclosed therein, human tissue plasminogen activator (t-PA) exists in both a single-chain and a two-chain form. The latter is a proteolytic derivative of the former. It has been shown that proteolytic conversion of the single-chain form to the two-chain form occurs during the lysis of a fibrin clot. Rijken, et al., *J. Biol. Chem.* 257, 2920 (1982).

Despite the profound advantages associated with natural t-PA as a clot-dissolving agent, it is not believed that the natural protein necessarily represents the optimal t-PA agent under all circumstances. Therefore, several variants have been proposed or devised to enhance specific properties of t-PA. Certain of those variants address disadvantages associated with the use of natural t-PA in situations where an agent with a longer half-life or slower clearance rate would be preferred, e.g., in the treatment of deep-vein thrombosis and following reperfusion of an infarct victim, or where a single-chain agent is preferred.

For further patent literature regarding modification of the protease cleavage site of t-PA, see, for example, EPO Pat. Nos. 241,209; EP 201,153 published Nov. 12, 1986; EP 233,013 published Aug. 19, 1987; EP 292,009 published Nov. 23, 1988; EP 293,936 published Dec. 7, 1988; and EP 293,934 published Dec. 7, 1988; and WO 88/10119.

SUMMARY OF THE INVENTION

The present application is directed to novel variants of t-PA, which surprisingly exhibit activity on par with or better than the human t-PA first isolated by Collen, et al., (EPO Publication No. 041766), as well as the t-PA molecules described in the aforementioned recombinant patent application. (EPO Publication No. 093619). In a particular embodiment, specific variants covered by the present invention include those having certain amino acid substitutions within the site surrounding positions 275 and 276 of the human t-PA amino acid sequence, occupied respectively by arginine and isoleucine. Certain enzymatically active molecules recognize this (these) site(s) (perhaps together with one or more adjacent amino acids) and functionally hydrolyze the bonds after basic amino acids, particularly between arginine/isoleucine and lysine/glycine, resulting in two-chain material. The two chains remain associated through disulfide bonding via cysteine residues. According to this embodiment of the present invention, for example, the substitution at these positions with amino acids other than, e.g., arginine and lysine, serves to produce variants wherein the respective cleavage sites are altered such that two-chain t-PA is not formed in vitro or in vivo or is formed at a reduced rate. Thus, this aspect of the present invention provides variant single-chain t-PAs for purposes of testing biological activity. It has been found that such variants are rendered immune, or at least resistant, to hydrolysis at the 275/276 site and that the resultant single-chain t-PA variants are unexpectedly on par with the activity of the Collen, et al., and/or recombinant t-PA molecules described above, in certain biological assays. Furthermore, indications are that such variants are less reactive with naturally occurring t-PA inhibitors.

Following more generally from the foregoing summary is contemplated with the present invention imparting the resistance to proteolytic degradation at any site recognized to be susceptible to such including, in addition to the specific most widely recognized site at amino acid site 275/276, the known sites at amino acids 27/28, 40/41 and 462/463.

Focusing with more particularity on the so-called one-chain, two-chain 275/276 site, this proteolytically susceptible cleavage site falls within a region defined by amino acids about 270 to about 279, or more preferably about 275 to about 279. Variations within this region makes it less, or not at all, susceptible to degradation creating a molecule that remains, with respect to this site, in single-, or one-chain, form. Further, destruction of the site by preferred variation at position 275, forming for example E275 t-PA, creates a molecule that may be susceptible (albeit at a considerably lower rate) to degradation (cleavage) at the 277/278 site. For this reason, further variation at the latter site creating, for example, I277 or E275I277 t-PA further protects the one-chain integrity of the molecule. Another embodiment is to modify the amino acid between those two 275/276 and 277/278 sites, namely, amino acid 276 preparing, as examples 276 t-PA variants, e.g., P276 t-PA, E275P276 t-PA, P276I1277 t-PA, and E275P276I1277 t-PA.

Further mutagenesis within the about 270 to about 279 region, or any other site, follows from the context of the present invention. The resulting variants may or may not be resistant to degradation by plasmin. The resulting variants can be characterized by one endpoint being measured by the susceptibility of cleavage(s) of the resultant, t-PA molecule, and/or another endpoint being measured by increased fibrin specificity.

Focusing on the broad 270–279 range, and more particularly the 275–277 range, particular variants disclosed herein are P276 t-PA, D276 t-PA, S276 t-PA, A276 t-PA, H276 t-PA, W276 t-PA, Y276 t-PA, etc., des or Δ275–277 t-PA, P insert at 275/276 t-PA, P276A277 t-PA, P276I1277 t-PA, etc.

More particularly, variants hereof solely at positions 275 and/or 277, and at no other position within the 275–277 range, or within the 270–279 broader range, include X275I276Z277 variants wherein X is an amino acid other than arginine (R) and Z is an amino acid other than lysine (K), or X is as defined and Z is lysine, or particularly, Z is as defined and X is arginine.

Also included within the scope of this invention are the associated compounds and means for preparing the variants hereof using the preferred mode of recombinant DNA technology, namely, DNA isolates encoding such variants, expression vectors, transfected host cells and processes for making and using each of them.

In yet another embodiment, the invention is directed to a composition for treating a vascular condition or disease comprising a therapeutically effective amount of the variant herein in admixture with a pharmaceutically acceptable carrier.

Also encompassed herein is a composition for preventing fibrin deposition or adhesion formation or reformation comprising a therapeutically effective amount of the variant herein in admixture with a pharmaceutically acceptable carrier.

In still another embodiment, the invention provides a method of treating a vascular condition or disease in a mammal comprising administering an effective amount of the appropriate composition described above to the mammal.

Another aspect of this invention is to obtain a t-PA molecule that is more fibrin specific so that it will act more preferentially at the site of the clot than unmodified t-PA.

BRIEF DESCRIPTION OF THE DRAWINGS

FIGS. 2a, b and c represent the DNA and amino acid sequences of t-PA including 5' and 3'-untranslated regions.

DETAILED DESCRIPTION

Figure 1:
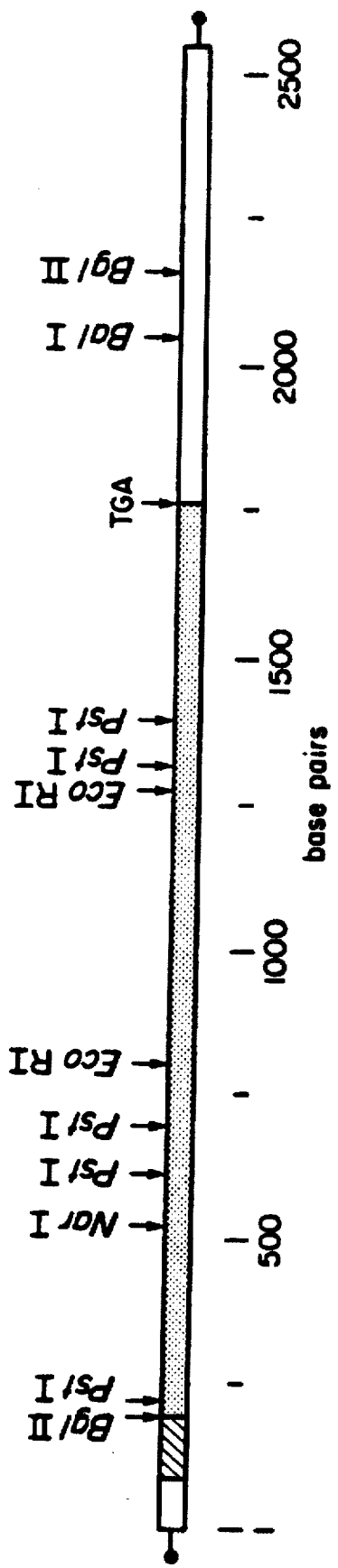
FIG. 1 is a restriction map of the DNA of human t-PA and includes 5' and 3'-untranslated regions as well as sequences encoding pre-t-PA. The speckled area represents the structure gene for t-PA.

As used herein, "tissue plasminogen activator", "human tissue plasminogen activator", "human t-PA", or "t-PA" denotes human extrinsic (tissue-type) plasminogen activator as produced, e.g., by recombinant cell culture systems, in bioactive forms comprising protease portion and corresponding to the plasminogen activator otherwise native to human tissue. It will be understood that natural allelic variations exist and occur from individual to individual, demonstrated by (an) amino acid difference(s) in the overall sequence. In addition, glycosylation patterns will depend on the nature of the host cellular environment.

Further, the terms contemplate "bioequivalent molecules" containing other amino acid differences in the overall sequence, beyond (naturally occurring) alleles. These may be purposefully introduced or result inadvertently such as via errors in cloning, etc.

As used herein, the term "wild-type t-PA" refers to the t-PA encoded by the cDNA reported by U.S. Pat. No. 4,766,075, supra, the disclosure of which is expressly incorporated herein by reference. The t-PA thus encoded is suitably a t-PA molecule from any native source or any recombinant expression system, including 293 or 294 cells, Chinese hamster ovary cells, etc.

It seems now clear that the human tissue plasminogen activator molecule contains five domains (stretches of amino acid sequence) that have been defined with reference to homologous or otherwise similar structures identified in various other proteins such as trypsin, chymotrypsin, plasminogen, prothrombin, fibronectin and epidermal growth factor. These domains have been designated, starting at the N-terminus of the amino acid sequence of human tissue plasminogen activator, as 1) the finger region (F) that has variously been defined as including amino acid 1 upwards of about 44, 2) the growth factor region (C) that has been variously defined as stretching from about amino acid 45 upwards of amino acid 91 (based upon its homology with EGF), kringle one (K1) that has been defined as stretching from about amino acid 92 to about 173, 4) kringle two (K2) that has been defined as stretching from about amino acid 180 to about amino acid 261 and 5) the so-called serine protease domain (P) that generally has been defined as stretching from about amino acid 264 to the C-terminal end of the molecule. These domains are situated contiguously generally of one another, or are separated by short "linker" regions, and account for the entire amino acid sequence from about 1 to 527 amino acids in its putative mature form.

A "two-chain cleavage site" in t-PA comprises at least the arginine residue at position 275. However, various amino acids adjacent to or within several residues of position 275, e.g., up to about 279, are also believed to be a part of the region recognized by enzymes which convert plasminogen activator to its two-chain form. Replacement of amino acids at positions other than or in addition to 275 within the region may be resistant to conversion to the two-chain form, and/or exhibit more fibrin specificity than wild-type t-PA.

In one particular embodiment, "single-chain plasminogen activator mutant" or "variant" is a plasminogen activator which is resistant to conversion to the two-chain form. It is characterized by single or multiple amino acid substitutions within the region defining the two-chain activation site. As modified, such activation site is not enzymatically recognized, and therefore, not hydrolyzed by enzymes which normally convert plasminogen activator to its two-chain form. In another embodiment, the variants may or may not resist hydrolysis but exhibit increased fibrin specificity.

A variety of methods may be used to induce mutations of underlying DNA so as to prepare the variants hereof. One such method, illustrated herein as a particularly preferred embodiment, comprises first inserting a fragment of the native t-PA gene, containing sequences coding for the region to be mutated, into the replicative form of phage M13mp8 to form M13mp8PA. A synthetic oligonucleotide, complementary to the inserted t-PA sequences but containing one or more nucleotide triplets which code for the amino acid to be substituted, is then annealed to the single stranded form of M13mp8PA to form a double stranded region. This region serves as a primer for DNA polymerase I synthesis of the remaining complementary strand. After replication and identification, the mutant t-PA sequence may be further modified or used to construct a prokaryotic or eukaryotic vector for expressing the mutated t-PA polypeptide.

As mentioned, the above described general method may also be used to mutate t-PA at positions other than the 275/276 and/or 277/278 two-chain cleavage sites, to produce mutated t-PA derivatives falling within the present invention. Such other positions are polypeptide sequences which are susceptible to enzymatic hydrolysis such as trypsin-like cleavage sites which typically comprise arginine or lysine followed by any amino acid except proline. Substitution of one or more amino acids within such trypsin-like cleavage sites results in mutant t-PAs which may resist hydrolysis by trypsin-like proteases. Such resistance to enzymatic degradation during expression and purification as well as during administration as a pharmaceutical agent results in a t-PA which does not lose biological activity as compared to the non-mutated t-PA. Examples of such trypsin-like cleavage sites within the human t-PA molecule include arginine-alanine (positions 40–41), arginine-serine (positions 27–28), and arginine-serine (positions 462–463).

The variant is assayed for its enzymatic activity by determining the kinetics of conversion of plasminogen to plasmin using the chromogenic plasmin substrate S-2251 in the presence of fibrin, fibrinogen (or fragments), using the assay described below.

The expression "fibrin specificity" refers to the activity of a variant that exhibits a higher ratio of fibrin-independent specific activity to fibrinogen-dependent specific activity in a S-2251 assay (in either the one-chain or two-chain form) than wild-type rt-PA, and preferably a ratio of at least 1.5.

As used herein, "transient expression system" denotes a cell culture containing cells transfected with a t-PA variant-encoding vector that expresses the DNA sequence encoding the variant transiently, i.e., in a manner that may not be stable. Such cells are deemed "capable of transient expression."

The t-PA variants herein, in addition to being altered from the native sequence at the 270–279 positions so as to display certain specific properties, also optionally contain substitutions, deletions, or insertions of residues in other regions of the native sequence of the molecule. These can be considered "bioequivalent molecules".

For example, the variants herein may be suitably devoid of at least a portion of the finger domain, the growth factor domain, and/or the kringle 1 domain, and/or devoid of glycosylation potential at the glycosylation site surrounding amino acid 184 and/or 117, and suitably contain amino acid modifications in the putative lysine binding site of kringle 1 or 2.

In addition, fibrin binding of t-PA can be modulated, most preferably restored or increased, by appropriate substitutions of positively or negatively charged amino acid residues on the opposite edges of the putative ligand binding pocket of the kringle 2 domain of t-PA. The variants herein are generally prepared by site-directed mutagenesis or by excision/ligation techniques described further hereinbelow.

Specific examples of such variants include a molecule devoid of amino acids 1 to 44 and a molecule having aspartic acid at position 184. Variants devoid of amino acids 1 to 44 are described more fully in WO 89/00197, supra.

The variants may also be modified such that a glycosylation site is inserted in the kringle-1 domain such as at position 103 (T103N). Other modifications can include one or more amino acid substitutions at positions 94 and/or 95 or from positions 293–305, or where the amino acids at positions 466–470 are deleted.

All of the above variants are optionally modified in various other regions of the molecule, if such modifications still satisfy the criteria expressed herein for specific characteristics. Such modifications include, for example:

1. Kringle 1 modifications, for example, deletion of about 92 to 179, and/or
2. Kringle 2 modifications, for example, deletion of about 174–261 or modification in the region of amino acids about 205–215, especially 210–213, and/or
3. Amino acids about 244–255, especially 252 or its site, and/or
4. Amino acids about 233–242, especially 236–238, and/or
5. Known glycosylation sites such as amino acid 184, and/or
6. Glycosylation within the growth factor domain, as described in copending U.S. application Ser. No. 07/196,909 filed May 20, 1988, the disclosure of which is incorporated herein by reference. Briefly, the t-PA molecule is N- or O-linked glycosylated within its growth factor domain, preferably at position 67–69, where the tyrosine at position 67 is replaced with an asparagine residue, to alter the half-life of the t-PA molecule.

Many of these modifications may significantly alter in vivo clearance rates and fibrin binding relative to native t-PA. The practitioner skilled in the art will be able to determine by the appropriate assay what the optimum properties of each variant are that are desired in any particular instance.

The modification to change or insert the appropriate amino acid(s) in the native molecule to effect the above sequence variations is accomplished by any means known in the art, such as, e.g., site-directed mutagenesis or ligation of the appropriate sequence into the DNA encoding the relevant protein, as described below.

For purposes of shorthand designation of t-PA variants hereof, it is noted that numbers refer to the amino acid residue/position along the 527 amino acid sequence of putative mature t-PA—see EPA 093619, which corresponds to U.S. Pat. No. 4,766,075. See also FIGS. 2a, 2b and 2c herein. Amino acid identification uses the single letter alphabet of amino acids, i.e.:

| Asp | D | Aspartic acid | Ile | I | Isoleucine |
| --- | --- | --- | --- | --- | --- |
| Thr | T | Threonine | Leu | L | Luecine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glkycine | Lys | K | Lysine |
| Ala | A | Alanine | Arg | R | Arginine |
| Cys | C | Cysteine | Trp | W | Tryptophane |
| Val | V | Valine | Gln | Q | Glutamine |
| Met | M | Methionine | Asn | N | Asparagine | and the number following such single letters refers to the amino acid position, e.g., E275 means a variant hereof having, inter alia, glutamic acid at position 275. Thus, E275I277 t-PA is the variant t-PA hereof having a glutamic acid at position 275 and an isoleucine at position 277. P276 is the variant t-PA hereof having proline at position 276.

Figure 17:
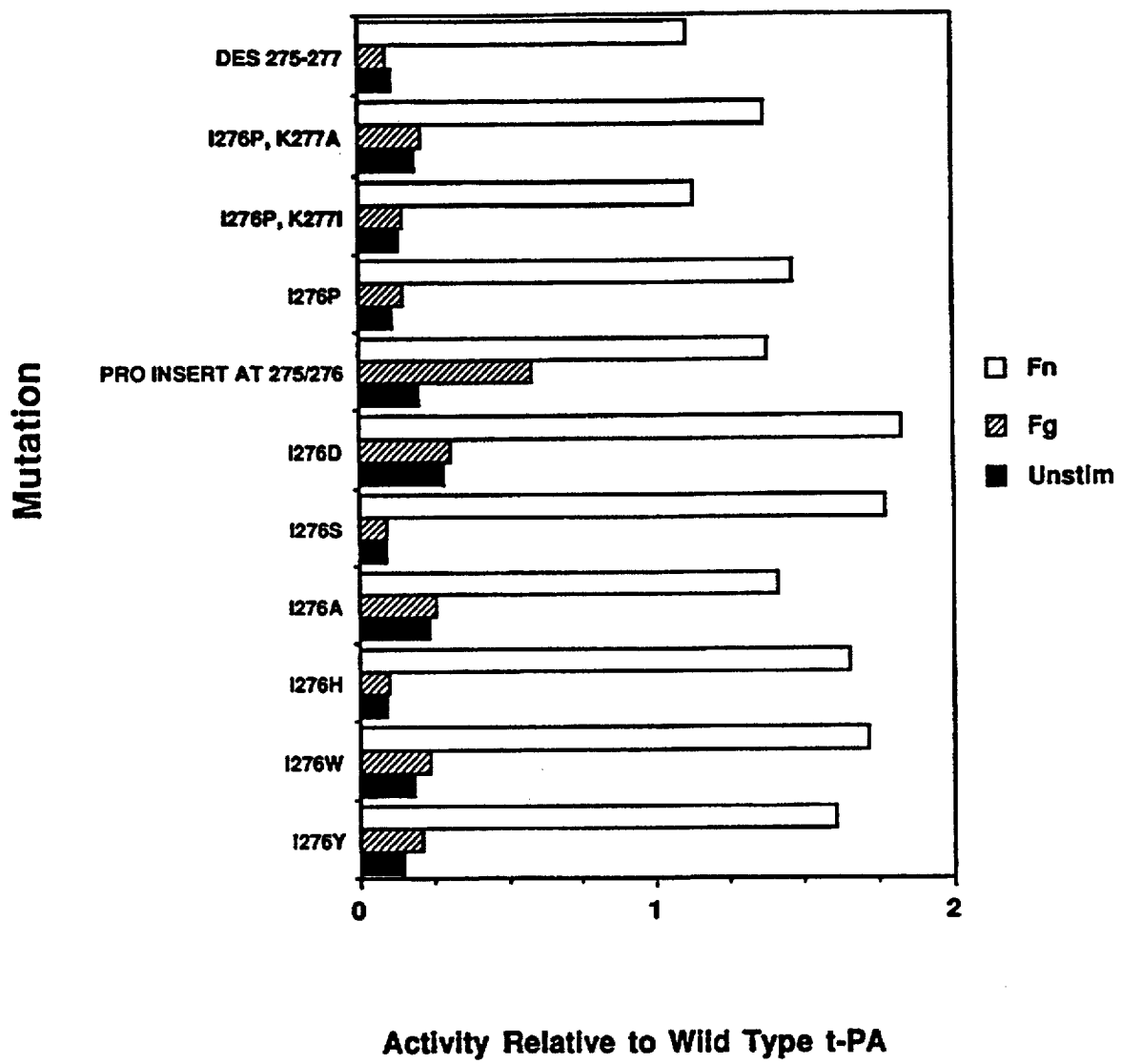
FIG. 17 depicts the activity of the t-PA variants at the 275–277 positions relative to wild-type t-PA (activity=1.0) in the S-2251 assay. In this figure, the letter appearing before the number is the natural amino acid at that numbered position and the letter appearing after the number is the variant amino acid at that position. Fn indicates the addition of fibrinogen and thrombin such that the assay is performed in the presence of fibrin. Fg indicates addition of fibrinogen alone. Unstim indicates only the t-PA variant and plasminogen are present in addition to the S-2251 substrate.

In certain instances, for example in FIG. 17, a somewhat different notation is employed, namely, the letter appearing before the number is the natural amino acid at that numbered position and the letter appearing after the number is the variant amino acid at that position. In this system, P276 would be expressed as I276P.

A. General t-PA derivatives hereof are prepared 1) having methionine as its first amino acid (present by virtue of the ATG start signal codon insertion in front of the structural gene) or 2) where the methionine is intra- or extracellularly cleaved, having its normally first amino acid, or 3) together with either its signal polypeptide or conjugated protein other than its conventional signal polypeptide, the signal polypeptide or a conjugate being specifically cleavable in an intra- or extracellular environment, or 4) by direct expression in mature form without the necessity of cleaving away any extraneous, superfluous polypeptide. In all events, the thus produced human mutated t-PA, in its various forms, is recovered and purified to a level suitable for the treatment of various vascular conditions or diseases such as myocardial infarct, strokes, pulmonary embolism, deep vein thrombosis, peripheral arterial occlusion and other thrombotic conditions.

Variant t-PA also has a functional definition in being capable of binding to fibrin and of mediating in vivo conversion of plasminogen to plasmin which in turn solubilizes fibrin clots.

"Expression Vector" includes vectors which are capable of expressing DNA sequences contained therein, where such sequences are operably linked to other sequences capable of effecting their expression and which are replicable in the host organisms, either as episomes or as an integral part of the chromosomal DNA.

"Recombinant host cells" refers to cells which have been transfected with expression vectors constructed using recombinant DNA techniques.

B. Host Cell Cultures and Vectors

The vectors and method disclosed herein are suitable for use in host cells over a wide range of prokaryotic and eukaryotic organisms. For example, E. coli K12 strain 294 (ATCC No. 31446) is particularly useful. Other microbial strains which may be used such as E. coli B, and E. coli X1776 (ATCC No. 31537). These examples are, of course, intended to be illustrative rather than limiting.

In addition to prokaryotes, eukaryotic organisms, such as yeast cultures, may be used. Cultures of cells derived from multicellular organisms are the hosts of choice currently. In principle, any such cell culture is workable; however, interest has been greatest in cells from vertebrates, and propagation of these cells in culture (tissue culture) has become a repeatable procedure—see Tissue Culture, Academic Press, Kruse and Patterson, editors (1973). Examples of such useful host cell lines re VERO and HeLa cells, Chinese Hamster Ovary (CHO) cell lines, e.g., DHFR$^+$ CHO-K1 cells (ATCC No. CCL 61), W138, BHK, COS-7, 293 and MDCK cell lines.

Examples which are set forth hereinbelow describe the use of E. coli using the trp promoter system and the use of CHO cells using expression vectors which include the SV40 Origin of replication as a promoter. However, it would be well within the skill in the art to use alternative prokaryotic or eukaryotic host cell cultures.

C. Methods Employed

1. Transfection

If cells without formidable cell wall barriers are used as host cells, transfection may be carried out by the calcium phosphate precipitation method as described by Graham, et al., Virology 52, 546 (1978). However, nuclear injection or protoplast fusion may also be used.

If prokaryotic cells or cells which contain substantial cell wall constructions are used, the preferred method of transfection is via calcium chloride as described by Cohen, et al., Proc. Natl. Acad. Sci. (USA) 69, 2110 (1972).

2. Vector Construction

Construction of suitable vectors containing the desired coding and control sequence employ standard ligation techniques known per se. Isolated plasmids or DNA fragments are cleaved, tailored, and re-ligated in the form desired to form the plasmids required.

3. Site-Specific Mutagenesis

Preparation of t-PA variants in accordance herewith is preferably achieved by site-specific mutagenesis of DNA that encodes an earlier prepared variant or a nonvariant version of the protein. Site-specific mutagenesis allows the production of t-PA variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman, et al., *DNA*, 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing, et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira, et al., *Meth. Enzymol.*, 153:3 (1987)) may be employed to obtain single-stranded DNA.

In general, site-directed mutagenesis in accordance herewith is performed by first obtaining a single-stranded vector that includes within its sequence a DNA sequence that encodes the relevant t-PA. An oligonucleotide primer bearing the desired mutated sequence is prepared, generally synthetically, for example, by the method of Crea, et al., *Proc. Natl. Acad. Sci.* (USA), 75:5765 (1978). This primer is then annealed with the single-stranded t-PA sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated t-PA region may be removed and placed in an appropriate vector for t-PA production, generally an expression vector of the type that typically is employed for transformation of an appropriate eukaryotic host. In the context of the present invention, Chinese hamster ovary (CHO) cells or 293 (human kidney cells described by Graham, et al., *J. Gen. Virol.*, 36:59 (1977)) are preferred for the preparation of long-term stable t-PA producers. However, the invention is not limited to CHO production, as it is known that numerous other cell types are suitably employed, particularly where one desires only transient production of the enzyme for test purposes. For example, described below is a transient system employing 293 cells that provides a convenient system for production of t-PA variants for analytical purposes.

4. Cleavage/Ligation Technique

Another method for making mutations in the DNA sequence encoding the t-PA involves cleaving the DNA encoding the t-PA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the t-PA-encoding DNA, thereby creating cohesive termini), and ligating the synthetic DNA into the remainder of the t-PA-encoding structural gene.

5. Host Cell Cultures and Vectors

Although Chinese hamster ovary (CHO) expression ultimately is preferred for t-PA production, the vectors and methods disclosed herein are suitable for use in host cells over a wide range of eukaryotic organisms.

In general, of course, prokaryotes are preferred for the initial cloning of DNA sequences and constructing the vectors useful in the invention. For example, *E. coli* K12 strain 294 (ATCC No. 31,446) and *E. coli* strain W3110 (ATCC No. 27,325) are particularly useful. Other suitable microbial strains include *E. coli* strains such as *E. coli* B, and *E. coli* X1776 (ATCC No. 31,537). These examples are, of course, intended to be illustrative rather than limiting.

Prokaryotes also are useful for expression. The aforementioned strains, as well as bacilli such as *Bacillus subtilis*, and other enterobacteriaceae such as, e.g., *Salmonella typhimurium* or *Serratia marcesans*, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar, et al., *Gene*, 2:95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang, et al., *Nature*, 375:615 (1978); Itakura, et al., *Science*, 198:1056 (1977); Goeddel, et al., *Nature*, 281:544 (1979)) and a tryptophan (trp) promoter system (Goeddel, et al., *Nucl. Acids Res.*, 8:4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist, et al., *Cell*, 20:269 (1980)).

In addition to prokaryotes, eukaryotic microbes, such as yeasts, also are suitably used herein. *Saccharomyces cerevisiae*, or common baker's yeast, is the most commonly used among eukaryotic microorganisms, although a number of other strains are commonly available. For example, for expression in Saccharomyces, the plasmid YRp7 (Stinchcomb, et al., *Nature*, 282:39 (1979); Kingsman, et al., *Gene*, 7:141 (1979); Tschemper, et al., *Gene*, 10:157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85:12 (1977) ). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255:2073 (1980)) or other glycolytic enzymes (Hess, et al., *J. Adv. Enzyme Reg.*, 7:149 (1968); Holland, et al., *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers, et al., *Nature*, 273:113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of human t-PA are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant t-PA and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci.* (USA) 77:4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

6. Typical Cloning and Expression Methodology Employable

If mammalian cells are used as host cells, transfection generally is carried out by the calcium phosphate precipitation method as described by Graham and Van der Eb, *Virology*, 52:546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75:1929–1933 (1978).

If prokaryotic cells or cells that contain substantial cell wall constructions are used, the preferred method of transfection is calcium treatment using calcium as described by Cohen, et al., *Proc. Natl. Acad. Sci.* (USA) 69:2110 (1972), or more recently electroporation.

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 µg plasmid or DNA fragments is used with about 1 unit of enzyme in about 20 µl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel, et al., *Nucleic Acids Res.*, 8:4057 (1980).

For ligation, approximately equimolar amounts of the desired components, suitably end tailored to provide correct matching, are treated with about 10 units T4 DNA ligase per 0.5 µg DNA. (When cleaved vectors are used as components, it may be useful to prevent religation of the cleaved vector by pretreatment with bacterial alkaline phosphatase.)

As discussed above, t-PA variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing, et al., *Nucleic Acids Res.*, 9:309 (1981) or by the method of Maxam, et al., *Methods of Enzymology*, 65:499 (1980).

After introduction of the DNA into the mammalian cell host and selection in medium for stable transformants, amplification of DHFR-protein-coding sequences is effected by growing host cell cultures in the presence of approximately 20,000–500,000 nM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In order to simplify the examples certain frequently occurring methods will be referenced by shorthand phrases.

"Plasmids" are designated by a low case p followed by an alphanumeric designation. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 2 units of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis, et al., 1982, *Molecular Cloning* pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn, et al., 1981, *Nucleic Acids Res.* 9:6103–6114, and D. Goeddel, et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, *J. Mol. Biol.* 98:503–517, and hybridization as described by T. Maniatis, et al., 1978, *Cell* 15:687–701.

"Transformation" or "transfection" means introducing DNA into an organism so that the DNA is replicable, either as an extrachromosomal element or chromosomal integrant. Unless otherwise provided, the method used herein for transformation of *E. coli* is the $CaCl_2$ method of Mandel, et al., 1970, *J. Mol. Biol.* 53: 154.

"Ligation" refers to the process of forming phosphodiester bonds between two double stranded nucleic acid fragments (T. Maniatis, et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis, et al., Id., p. 90, may be used.

"Oligonucleotides" are short length single or double stranded polydeoxynucleotides that are chemically synthesized by known methods and then purified on polyacrylamide gels.

D. Pharmaceutical Compositions

The compounds of the present invention can be formulated according to known methods to prepare pharmaceutically useful compositions, whereby the t-PA product hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo, et al., the disclosure of which is hereby incorporated by reference. Such compositions will typically contain an effective amount of the variant herein, for example, from about 0.5 to about 5 mg/ml, together with a suitable amount of carrier vehicle to prepare pharmaceutically acceptable compositions suitable for effective administration to the host. The t-PA variant herein may be administered parenterally to subjects suffering from cardiovascular diseases or conditions, or by other methods that ensure its delivery to the bloodstream in an effective form.

Compositions particularly well suited for the clinical administration of variant t-PA products employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, on the order of about 0.05 to about 0.2 mg/kg, will typically be preferred with subsequent administrations, on the order of about 0.1 to about 0.2 mg/kg, being given to maintain an approximately constant blood level, preferably on the order of about 3 µg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of about 0.3 mg/kg.

For example, the t-PA variant hereof is suitably administered parenterally to subjects suffering from cardiovascular diseases or conditions. Dosage and dose rate may be parallel to or higher than that currently in use in clinical investigations of other cardiovascular, thrombolytic agents, e.g., about 1–2 mg/kg body weight as an intravenous or intra-arterial dose over 1.5 to 12 hours in human patients suffering from myocardial infarction, pulmonary embolism, etc. Higher doses may be tolerated because the variants herein have lower side effects than wild-type t-PA, leading to faster and more complete clot lysis.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variants herein also are useful to prevent fibrin deposition or adhesion formation or reformation. One embodiment of this use is described in copending U.S. Ser. No. 07/125,319 filed Nov. 25, 1987, the disclosure of which is incorporated herein by reference. Generally, such treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Typically, this amount is from 0.02 mg/g of gel to 25 mg/g of gel, with preferred amounts from 0.20 mg/g gel to about 2.5 mg/g of gel, most preferably from 0.25 mg/g to about 1.0 mg/g of gel.

The vehicle in which the t-PA is typically formulated for preventing adhesion formation in a semisolid, mucilaginous pharmaceutically inert carrier for positioning the enzyme at the site of potential adhesion formation. Such a carrier includes long-chain hydrocarbons or vegetable oils and waxes composed of mixtures of saturated and unsaturated fatty acid glycerides or mixtures of modified saturated and unsaturated fatty acid glycerides. Examples include semisolid vehicles such as petroleum jelly or semi-synthetic glycerides, polyhydroxy solvents such as glycerol, long-chain hydrocarbons, bioerodable polymers, or liposomes.

The following examples are intended merely to illustrate the best mode now known for practicing the invention, but the invention is not to be considered limited thereto.

All literature and patent application citations herein are expressly incorporated by reference.

E. Examples

Example 1

1. Construction of M13mp8PABglII For t-PA Mutagenesis

Human t-PA DNA was obtained from plasmids pPADHFR-6 (also designated pETPFR) and pPA25E10. The preparation of these two t-PA plasmids is described in EPO Application Publication No. 093619, referred to above and incorporated herein by reference. Superfluously, these two plasmids, and in transfected form, have been deposited with the American Type Culture Collection, Rockville, Md., USA as follows: pETPFR—ATCC Nos. 40403 and CRL 9606- and pPA25E10—ATCC Nos. 40401 and 67587.

Plasmid pPA25E10 contains sequences coding for the last 508 amino acids of the t-PA gene and 772 base pairs of the 3' untranslated region. This plasmid was digested with SacI and BglII to produce a 744 base pair fragment which was isolated by standard methods as previously described. As can be seen from the known sequence and restriction map of t-PA in FIGS. 1 and 2, this fragment contains the codons for t-PA amino acids 411 through 527 and includes part of the 3' untranslated region.

Plasmid pPADHFR-6 contains the entire structural gene for t-PA and part of the 3' untranslated region. This plasmid was digested with SacI and BglII to produce a 1,230 base pair fragment which was isolated. This fragment contains codons for the first 410 amino acids of the mature form of t-PA.

These fragments were ligated together using standard methods and digested with BglII. A 1,974 base pair fragment containing codons for the entire mature t-PA sequence plus part of the 3' untranslated region was isolated. Double stranded M13mp8, (Messing, et al., Third Cleveland Symposium on Macromolecules Recombinant DNA, Editor A. Walton, Elsevier, Amsterdam (1981), p. 143) was digested with BamHI and annealed to the BglII digested t-PA to form M13mp8PABglII. E. coli JM 101 cells (ATCC No. 33876) were transformed with the double stranded replicative form of M13mp8PABglII. The single stranded and double stranded (RF) forms of M13mp8PABglII may be isolated from E. coli JM 101 cells infected with this phage. The single stranded form was used for the site specific mutagenesis of t-PA.

2. Synthesis of Primers for Site Specific Mutagenesis

The human t-PA structural gene was modified by site specific mutagenesis to express t-PAs with amino acid substitutions at various positions. Synthetic oligonucleotides were prepared such as by the solid phase phosphotriester method of Crea, et al., *Proc. Natl. Acad. Sci. USA* 75, 5765 (1978). The following synthetic primers were prepared and used for such site specific mutagenesis:

| | | | | 270 | | | | 279 |
|---|---|---|---|---|---|---|---|---|
| Native Amino Acid Sequence | Pro | Gln | Phe | Arg (R)* | Ile | Lys (K) | Gly | Gly |
| Native DNA Sequence | G CCT | CAG | TTT | CGC | ATC | AAA | GGA | G |
| Primer 1B8 DNA Sequence | G CCT | CAG | TTT | Gly(G) GGT | ATC | Lys(K) AAA | GGA | G |
| Primer 2C9 DNA Sequence | G CCT | CAG | TTT | Glu(E) GAA | ATC | Lys(K) AAA | GGA | G |
| Primer 4A10 DNA Sequence | G CCT | CAG | TTT | Arg(R) CGC | ATC | Ile(I) ATC | GGA | G |
| Primer 3A7 DNA Sequence | G CCT | CAG | TTT | Gly(G) GGT | ATC | Ile(I) ATC | GGA | G |
| Primer 4B3 DNA Sequence | G CCT | CAG | TTT | Glu(E) GAA | ATC | Ile(I) ATC | GGA | G |

*single letter alphabet of amino acids

The amino acid and gene sequence of native t-PA is depicted in the first two lines. The primers have triplets which differ from the native gene sequence at the residue shown. The corresponding amino acid substitution is shown above the triplet coding for that amino acid.

3. Site Specific Mutagenesis

The procedure described hereinafter, was used to generate different t-PA clones containing the mutated sequence of the synthetic primers. The general method used is that of Adelman, et al., *DNA* 2 183 (1983), incorporated herein by reference. The overall scheme to generate each of these clones is presented in FIG. 3. M13RF1B8, 3M13RF2C9 and M13RF4A10 were generated by the use of primers containing mutations for the single amino acids shown. Single standard M13RF4A10, containing a mutation at position 277, was annealed with primer 3A7 or 4B3 to generate M13RF3A7 nd M13RF4B3 respectively. Purified M13 RF DNA from each of these mutated t-PA genes was prepared from E. JM 101 cells. Subsequently, DNA fragments containing the mutated t-PA DNA sequence were used to construct expression vectors for the mutated t-PA.

50 ng of a synthetic oligonucleotide was phosphorylated for 30 min at 37° C. in 10 μl of 50 mM Tris-HCl pH 7.5, 10 mM MgCl$_2$, 10 mM dithiothreitol, 1 mM ATP containing 8 U of T4 polynucleotide kinase. For use as a probe, 400 ng of the synthetic oligonucleotide was phosphorylated as above except that ATP was replaced with 60 mCi [γ$^{32}$-P]-ATP (3000 μCi/mmol) resulting in approximately 50 to 60×10$^6$ cpm/400 ng of 24-mer. For heteroduplex formation, 10 ng single stranded M13mp8PABglII was heated to 95° C. (10 min), and slowly cooled to room temperature (30 min) in 40 μl 10 mM Tris-HCl pH 7.5, 10 mM MgCl$_2$, 1 mM dithiothreitol containing 10 ng of the phosphorylated primer and 50 ng of EcoRI-digested M13mp8PABglIIRF large fragment. Primer extension was started by the addition of 10 μl ligase buffer containing 2 mM ATP, 0.25 mM each of dGTP, dTTP, dCTP and dATP, 5 U of *E. coli* DNA polymerase I large fragment and 400 U of T4 DNA ligase. After 1 hr at 12° C. the reaction mixture was used to transform *E. coli* JM 101 cells.

Transformation was accomplished by mixing 10 μl of the ligation mixture with 200 μl of competent JM 101 cells, followed by incubation for 30 min on ice and 5 min at 37° C. Then 3.5 ml 2YT top agar at 55° C. was mixed with 300 μl saturated JM 101 cells, 10 μl IPTG (200 mM) and 50 μl Xgal and after addition of the transformed cells plated on 9 cm Petri dishes containing LB with no drugs.

Colorless placques were picked and transferred to microtiter dish containing 100 μl 2YT medium. The inoculated microtiter fluids were stamped on 15 cm diameter LB agar plates overlayed with a lawn of 600 μl JM 101 cells in 8 ml 2YT top agar and incubated overnight at 37° C. The formed plaques were transferred to a nitrocellulose disc by physical contact for 1 min. The nitrocellulose disc was treated with 0.5M NaOH, 1.5M NaCl for 3 min and washed twice with 3M NaCl-0.5M Tris HCl pH 7.5 for 15 min and then with 2×SSC for 15 min. Prehybridization mix contains 10 mM Tris pH 7.5, 5 mM EDTA, 0.9M NaCl, Denhardt 0.5 percent NP40, 100 μM ATP, 1 mM sodium pyrophosphate, 1 mM sodium phosphate and 50 μg/ml *E. coli* tRNA. 1×Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of 5×10$^6$ cpm labeled primer and hybridized overnight. Selective washing of the disc was performed with 0.4×SSC at 49° C. and after air-drying the disc was exposed to X-ray film. Positively hybridizing clones were further analyzed by dideoxy sequencing. See Aldeman, Ibid.

Figure 4:
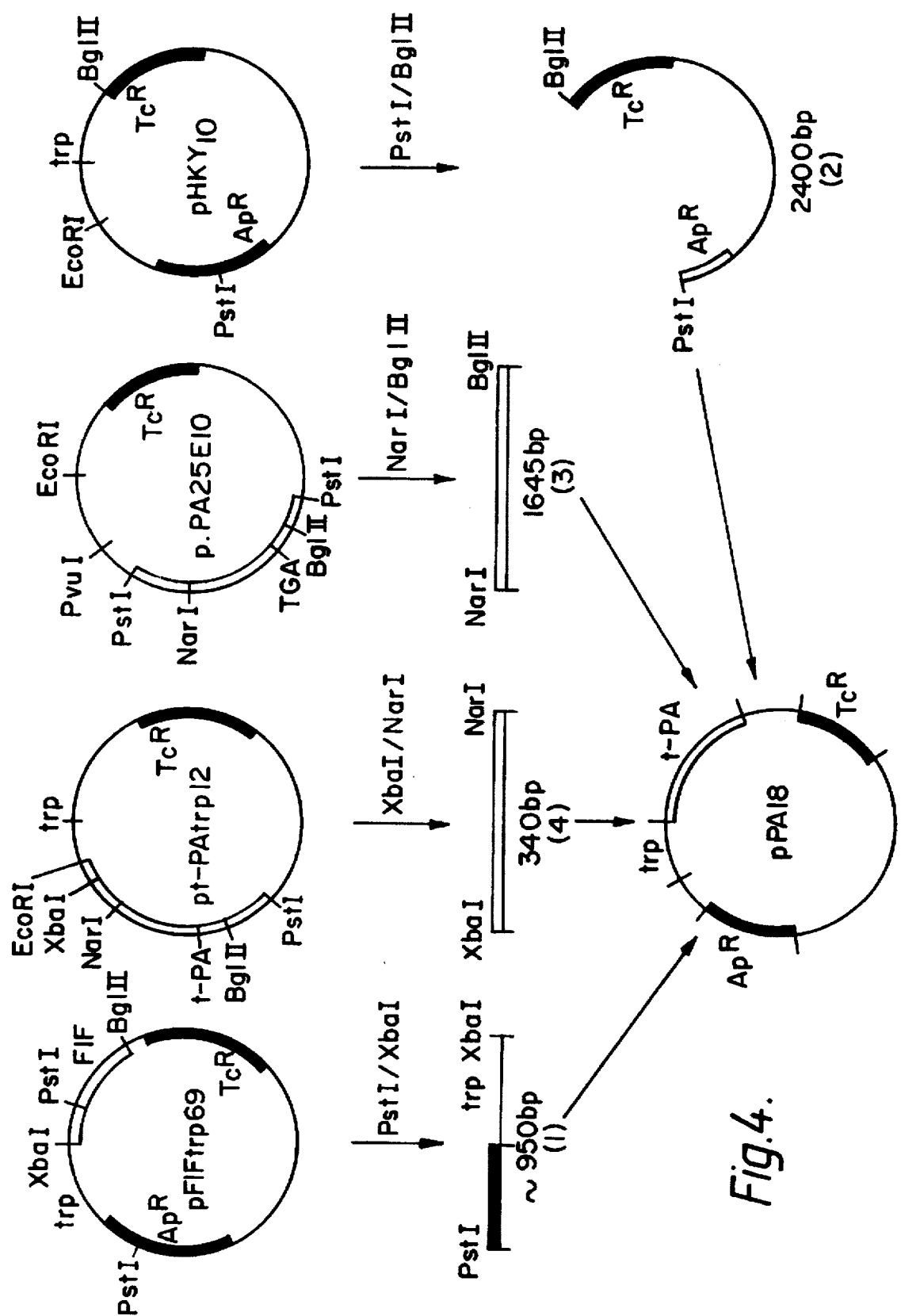
FIGS. 4 through 8 depict the construction of pXAPPA18 3'ΔX10trpR.
Figure 5A:
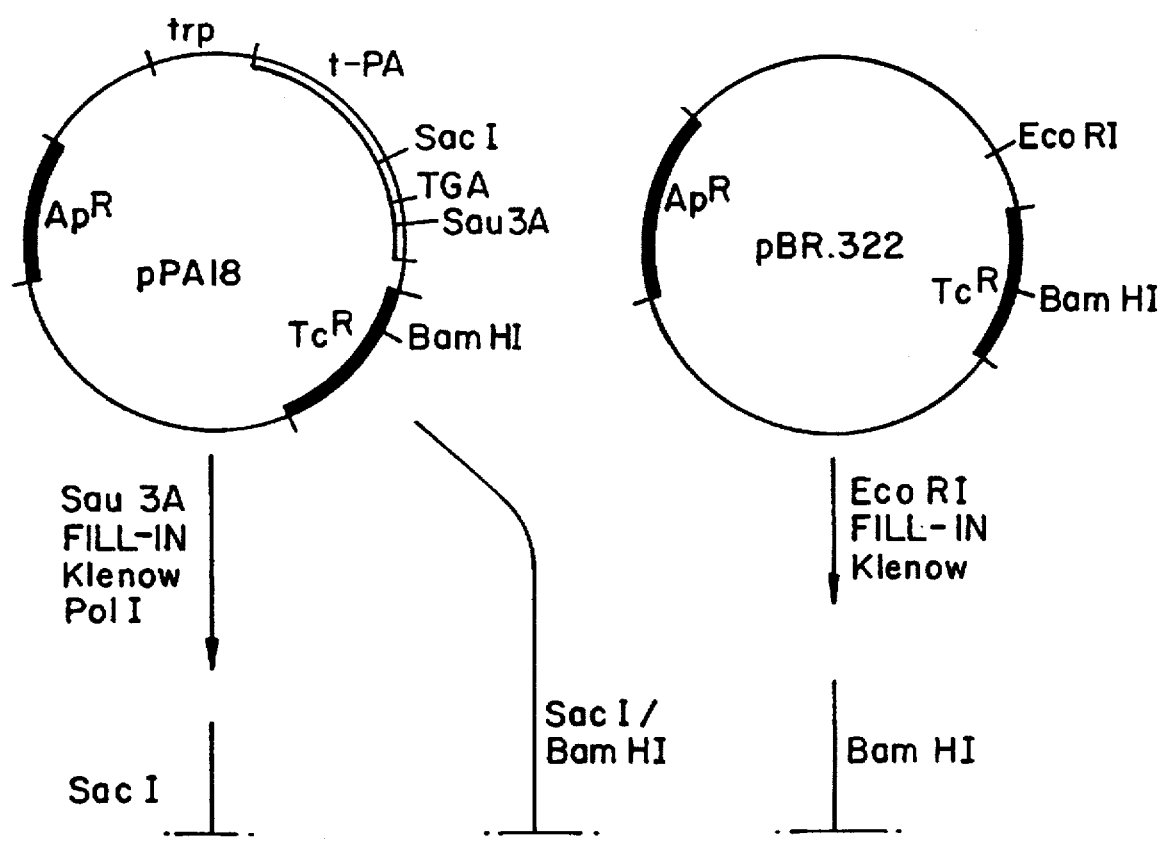
Figure 5B:
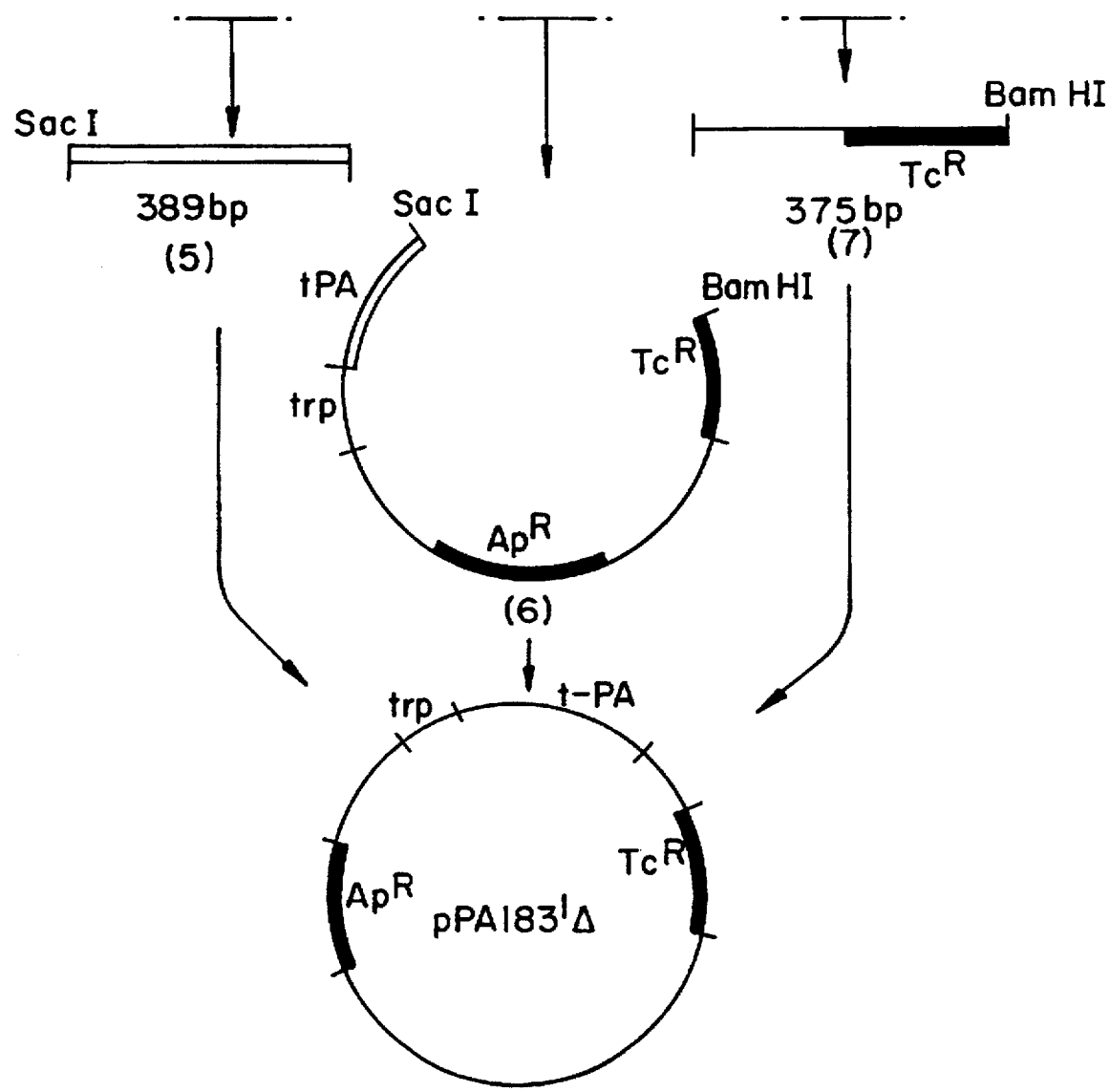

4. Construction of Vectors for Expression of Mutant t-PA *E. coli* pXAPPA18 3'Δx10trpR The plasmid pXAPPA18 3'Δx10trpR plasmid was constructed for use as an expression vector for the various mutated t-PA DNA sequences. The overall scheme used for construction of this plasmid is depicted in FIGS. 4 through 8. The resulting plasmid is depicted in FIG. 8. It contains the trpR repressor gene and a deletion of pBR322 DNA sequences which inhibit plasmid amplification. This deletion, known as XAP deletion, consists of the removal of 641 base pairs of pBR322 DNA sequences between the AvaI and PvuII restriction sites of pBR322 as disclosed by Sutcliff, Cold Spring Harbor Symposium on Quantitative Biology, Vol. 43, 77 (1979) Cold Spring Harbor Press, incorporated herein by reference. The trpR repressor gene compensates for the premature derepression of t-PA expression caused by increased plasmid copy number. Intermediate to the construction of pXAPPA18 3'ΔA10trpR is the plasmid pPA18 which was constructed as depicted in FIG. 4. This plasmid contains the entire pre-t-PA structural gene as well as 5' and 3' on untranslated regions. A promoter associated with the t-PA gene and sequences conferring ampicillin and tetracycline resistance are also characteristic of this plasmid.

In order to construct pPA18, four plasmids were used, namely pFIFtrp69, pHKY10, ptPAtrp12 and pPA25E10. Plasmid pFIFtrp69 is disclosed in Goeddel, et al., *Nucleic Acids Res.* 8, 4057 (1980). Plasmid pHKY10 is disclosed in U.S. patent application Ser. No. 685,521 filed 24 Dec. 1984 which is a continuation of U.S. Ser. No. 307,473 filed 1 Oct. 1981 which is a continuation of Ser. No. 133,296 filed 24 Mar. 1980, all now abandoned. One application in this series of applications has issued as U.S. Pat. No. 4,663,283 and corresponds in text to the European patent application referred to in the following parenthetical text. (European Patent Application Publication No. 0036776). Plasmids ptPAtrp12 and pPA25E10 are disclosed in Pennica, et al., *Nature* 301, 214 (1983), and in EPO Publication No. 093, 619. Generally, the plasmid pFIFtrp69 is digested with PstI and XbaI to produce the 950 base pair fragment designated fragment 1 in FIG. 4. The plasmid ptPAtrp12 was digested with XbaI and NarI. From this the 340 base pair sequence designated fragment 4 in FIG. 4 was isolated. The plasmid pPA25E10 was digested with NarI and BglII. From this was isolated the 1604 base pair fragment designated fragment 3 in FIG. 4. The plasmid pHKY10 was digested with PstI and BglII to produce a 2900 base pair fragment designated fragment 2 in FIG. 4. These four fragments were ligated and this DNA used to transform *E. coli* cells to give pPA18.

The plasmid pPA18 was isolated and digested with Sau3A followed by treatment with the Klenow fragment of DNA polymerase I to fill in the restriction site. The non-circular plasmid was treated with SacI and a 389 base pair sequence designated fragment 5 in FIG. 5 was isolated. Plasmid pPA18 was also digested with SacI and BamHI. From this the vector fragment 6 was isolated. The plasmid pBR322, Boyer, et al., *Gene* 2, (1977), was digested with EcoRI followed by treatment with the Klenow fragment of DNA polymerase I. This open-ended DNA sequence was treated with BamHI to produce the 375 base pair sequence depicted as fragment 7 in FIG. 5. Fragments 5, 6 and 7 were ligated and this preparation used to transform *E. coli* from which the plasmid pPA183'Δ was obtained. This plasmid is equivalent to pPA18 except that part of the 3' untranslated region of the t-PA gene has been removed.

Figure 6:
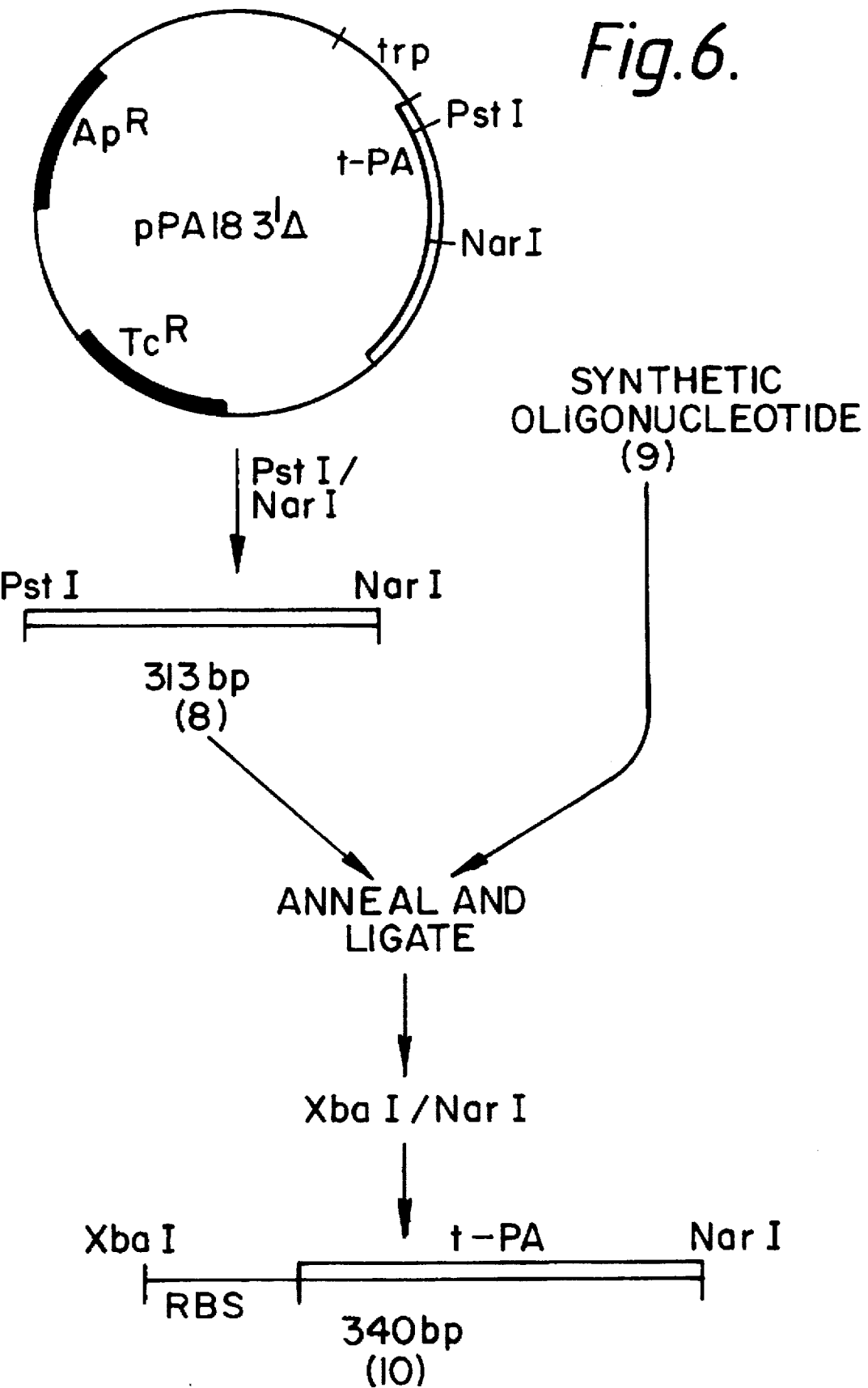

The plasmid pPA183'Δ A was digested with PstI and NarI to produce a 313 base pair fragment designated fragment 8 in FIG. 6. This fragment encodes amino acids 8 through 109. Synthetic oligonucleotide fragment 9 has the following sequence:

5' CTAGAATTATGTCTTATCAAGTTATTTGCATTAATACA-
GAATAGTTCAATAA 5'

This synthetic DNA was ligated to the PstI site of fragment 8 to regenerate the arginine codon at position 7 and the first six amino acid codons of the mature t-PA molecule. In addition, a ribosome binding site was positioned 5' to the synthetic N-terminal methionine codon positioned immediately 5' to residue 1 of the mature t-PA amino acid coding sequence. The 5' end of this oligonucleotide contains an XbaI restriction site. Thus, fragment 8 was ligated in the presence of the synthetic oligonucleotide fragment 9 and the mixture treated with XbaI and NarI to give fragment 10 (see FIG. 6).

Figure 7A:
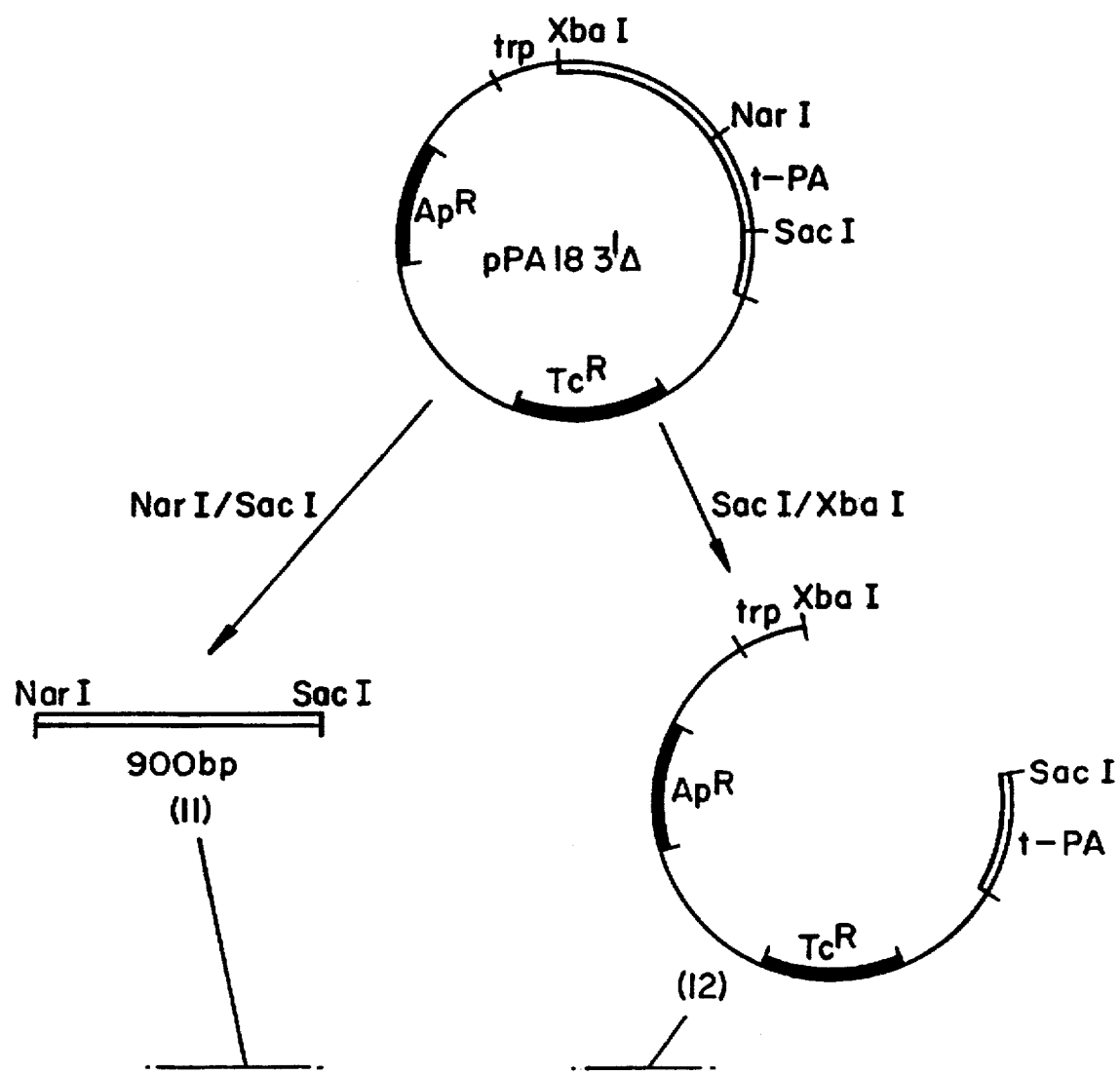
Figure 7B:
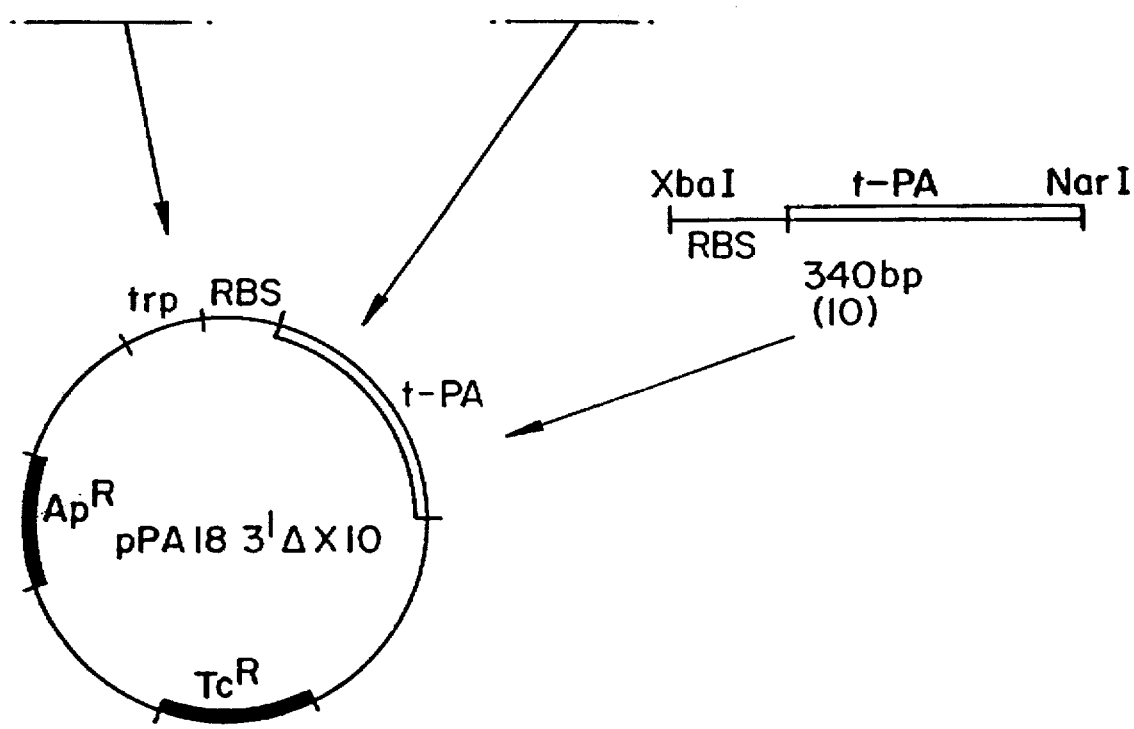
Figure 8A:
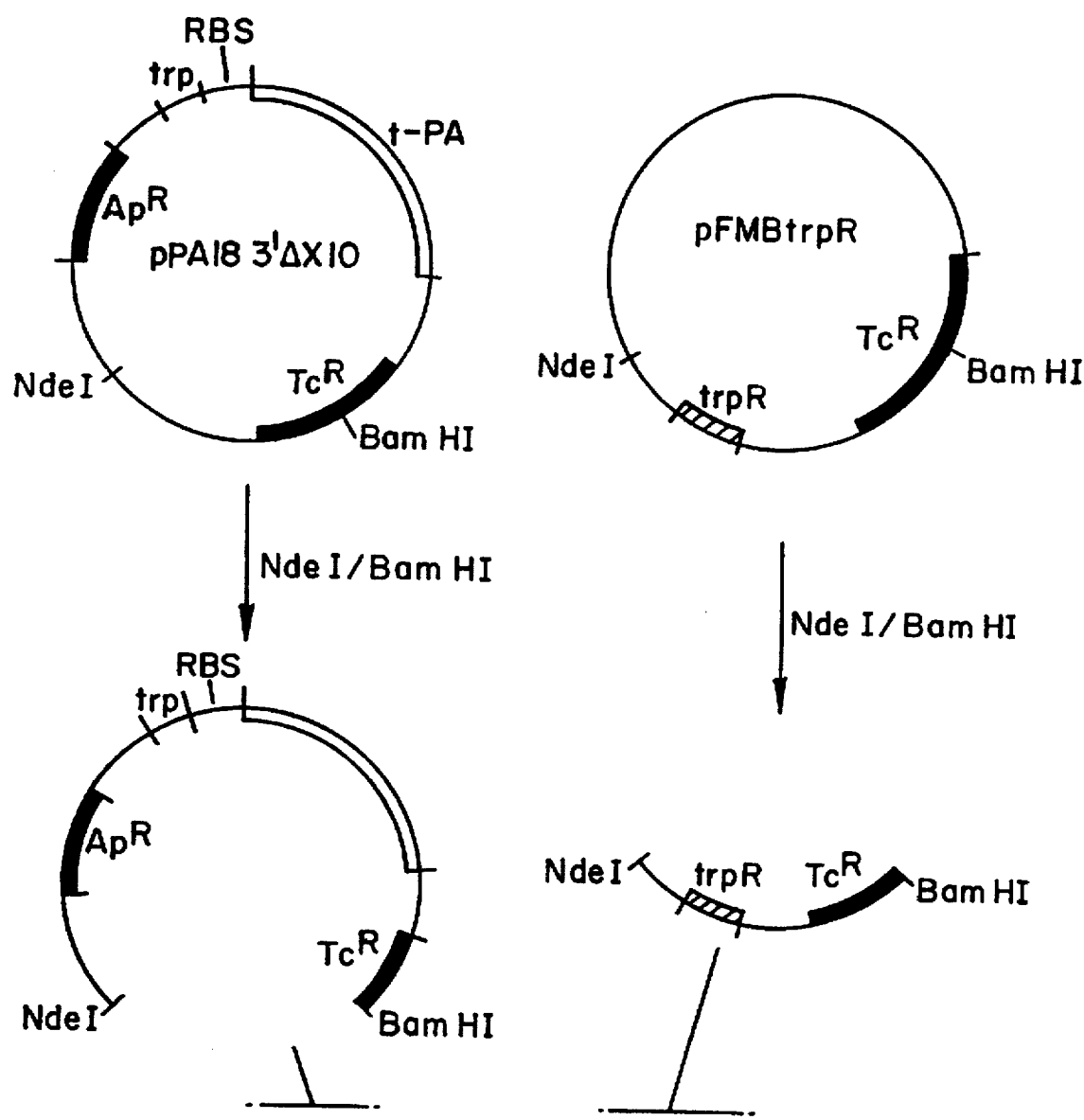
Figure 8B:
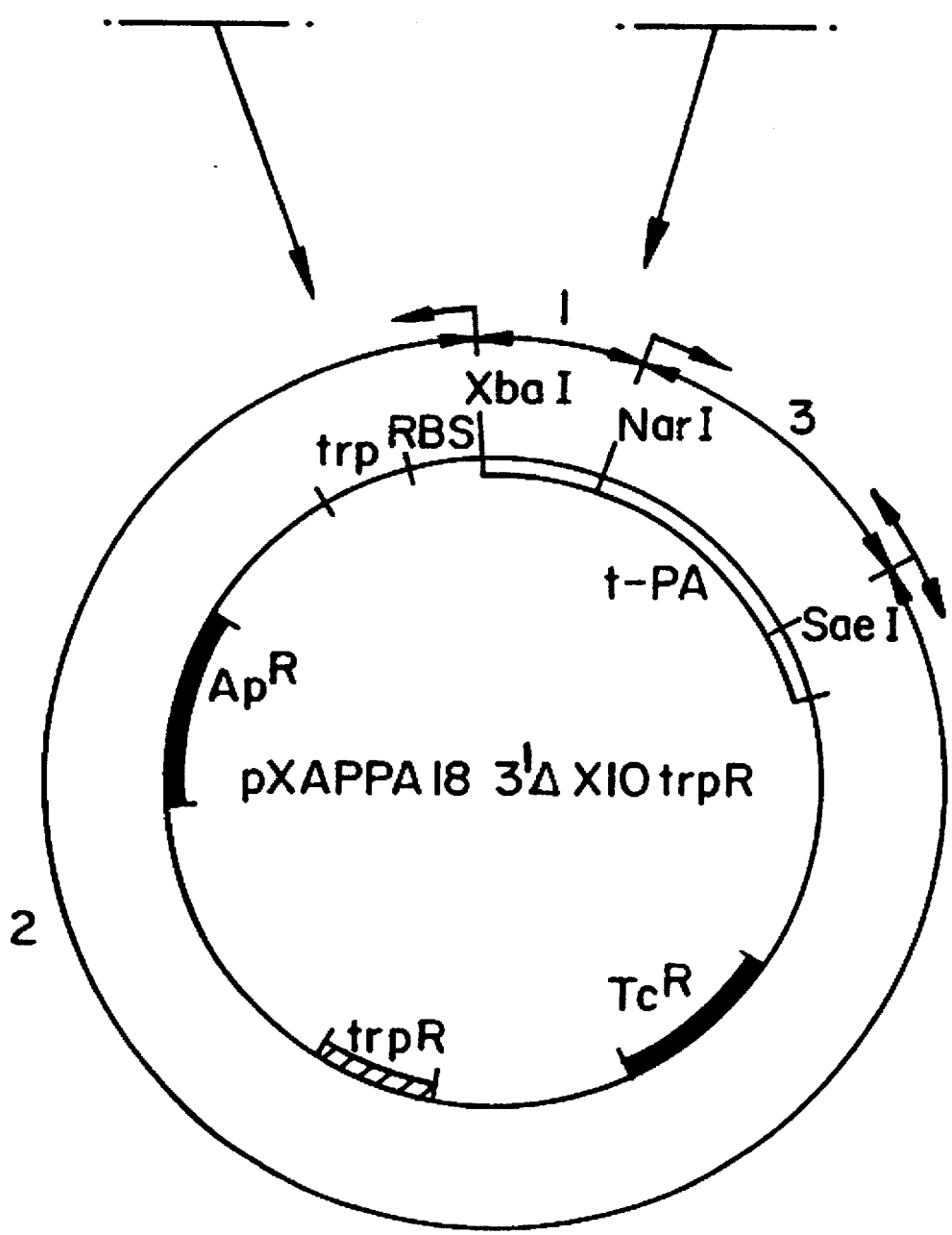

Plasmid pPA183'Δ was digested with NarI and SacI to produce the 900 base pair sequence designated fragment 11 in FIG. 7. This plasmid was also digested with SacI and XbaI to produce vector fragment 12 in FIG. 7. Fragment 10, 11, and 12 were ligated and used to transform *E. coli* from which was isolated pPA183'ΔX 10. A DNA sequence containing the XAP deletion and trpR repressor gene is derived from pFMBtrpR which is disclosed in U.S. patent application Ser. No. 538,730 filed 3 Oct. 1983, now abandoned (EPO Publication No. 136907). Briefly, this plasmid was constructed from three plasmids known to those skilled in the art: phGH107, described in EPO Publication No. 022242, published 14 Jan. 1981, was used as a source for the lac inducible promoter; ptrpR3, described in Roeder, et al., *Molecular Genetics* 176, 361 (1979) was used as the source of the coding sequence for trp repressor and pFMB1, described in EPO Publication No. 0068693 published 5 Jan. 1983, was used as the source of the coding sequence for the FMD antigen derived from strain A24.

To obtain the trp repressor sequence, ptrpR3 was treated with HaeIII, and the 334 base pair fragment was isolated from a 6 percent acrylamide gel and the isolated fragment was ligated with 16-mer EcoRI linkers having the sequence:

5' CCATAGAATTCTATGG.

To obtain vector backbone and the lac promoter, phGH107 was first digested with EcoRI and treated with bacterial alkaline phosphatase. The large vector fragment containing the lacUV5 promoter was then ligated to the tailored trpR plasmid using T4 ligase, and the ligation mixture transformed into *E. coli*. Plasmid DNA from transformants was isolated and the presence of the desired plasmid, designated ptrpR/hGH 107, confirmed. Messing, et al., *Nucleic Aids Res.* 9, 309 (1981).

ptrpR/hGH107 was partially digested with EcoR1, blunt ended using Klenow, treated with PvuII to provide the lac promoter/trp repressor operon (the 530 b.p. fragment). Partial PvuII digestion of pFMB1 and isolation of vector fragment on 6 percent polyacrylamide provided the expression vector backbone containing the FMB coding sequence under control of the trp promoter. The ptrpR/hGH107 fragment was mixed with the pFMB1 PvuII digest and ligated with T4 ligase. The ligation mixture was then used to transform *E. coli* strain 294, and transformants used as a source of plasmid DNA. The resulting plasmid, pFMB/trpR was verified by miniscreen, and for orientation of the insert by AvaI/PvuII digestion. Plasmid pFMB/trpR was digested with NdeI and BamHI. The fragment containing the trpR repressor was isolated. Plasmid pPA183'ΔX10 was digested with NdeI and BamHI. The main vector fragment was isolated. This vector fragment and trpR repressor fragment from pFMB trpR were ligated and the DNA mixture used to transform *E. coli* which the plasmid pXAPPA183'ΔX10trpR was isolated, as shown in FIG. 8.

5. *E. coli* Expression Vectors for t-PA Mutants

Figure 3:
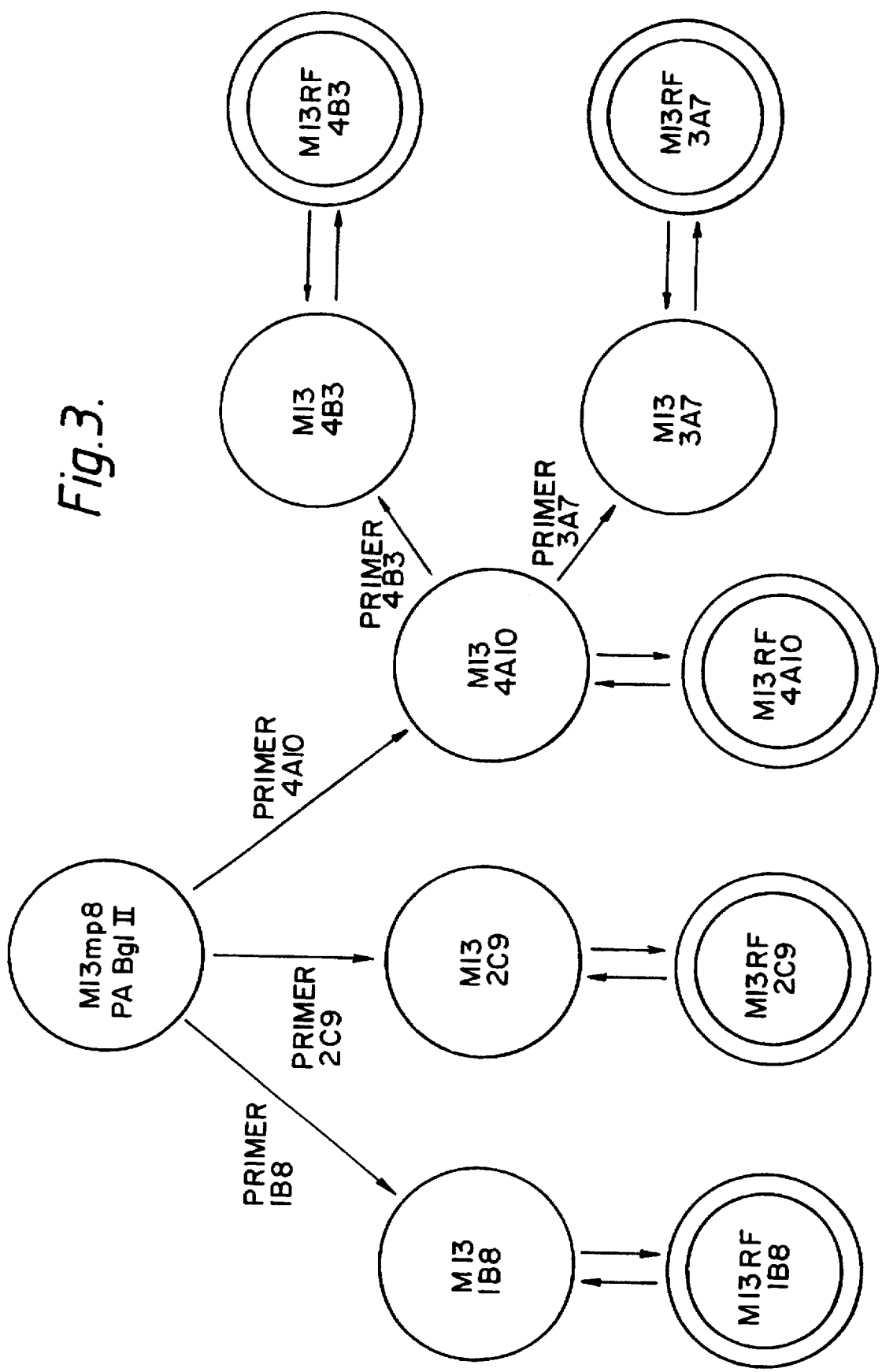
FIG. 3 is the overall scheme used to generate individual clones containing substitutions at position 275.

FIG. 8 depicts the pXAPPA183'Δx10trpR vector used to express t-PA and t-PA mutants in *E. coli*. As can be seen, the expression of the native t-PA structural gene is controlled by the trp promoter. Attention is directed to the XbaI, NarI and SacI restriction sites. Plasmid pXAPPA183'x10trpR was digested with NarI and XbaI. A 340 base pair fragment identified as fragment 1 in FIG. 8 was isolated. A vector fragment identified as fragment 2 in FIG. 8 was obtained by isolating the large fragment obtained by digestion of pXAPPA183'Δx10trpR with XbaI and SacI. Fragment 3 (900 bp) was obtained by digesting with NarI and SacI RF DNA of each of the mutant t-PA M13 clones, obtained by site specific mutagenesis. (FIG. 3). Vectors expressing different mutant t-PAs were obtained by ligating fragments 1 and 2 with the respective fragments 3 and used to transform *E. coli* from which were isolated each of the *E. coli* mutant t-PA expression vectors:

pXAPPA18 3'Δx10trpR 1B8
pXAPPA18 3'Δx10trpR 2C9
pXAPPA18 3'Δx10trpR 4A10
pXAPPA18 3'Δx10trpR 3A7
pXAPPA18 3'Δx10trpR 4B3

These plasmids, as well as the wild type t-PA expression vector pXAPPA183'Δx10trpR were used to transform *E. coli* W3110fhuA⁻.

*E. coli* W3110 fhuA⁻ is a T1 phage resistant bacterium characterized by a deletion or inversion of DNA sequences associated with the fhuA gene as disclosed in co-pending U.S. patent application Ser. No. 06/673,955 filed 11 Nov. 1984.

Briefly, *E. coli* W3110 (ATTC 27325) is transduced with lambda bacteriophage containing the transposable element Tn10 which confers tetracycline resistance. Strains of Tn10 transduced W3110 are selected for resistance to phage infection. Phage resistant strains are pooled and infected with bacteriophage P1. The resulting lysate is used to transduce *E. coli* AT982 (Bukhari, et al., *J. Bacteriology* 105, 844 (1971)). Strain AT 982 contains a Dap mutation located close to the fhuA gene. Accordingly, transduction of strain AT 982 by the P1 lysate and selection of transductants which are tetracycline resistant and which regenerate the DAP function indicates that transposon Tn10 is located within the fhuA gene. Strains which are tetracycline resistant and demonstrate regenerated DA function are the source of DNA for bacteria phage P1 transduction of *E. coli* W3110. Transduced W3110 strains expressing tetracycline resistance and phage resistance are selected. These strains are then selected on the basis of resistance to phage infection and reversion to tetracycline sensitivity. Naloy, et al., *J. Bacteriology* 145, 1110 (1981). The reversion to tetracycline sensitivity coupled with the retention of resistance to T1 phage infection indicates that DNA sequence associated with the fhuA gene have either been deleted or inverted irreversibly. Strains so constructed are designated *E. coli* W3110 fhuA⁻.

The phage containing the transposable element Tn10 which was used to insert Tn10 into W3110 was constructed as follows. The starting material was lambda cI857b 2210am29. This phage is known to those skilled in the art Kleckner, *J. Mol Biol.* 116, 125 (1977), and was constructed from three well-known mutants of lambda by standard procedures. A lysate of this lambda phage was prepared on the amber suppressor *E. coli* C600 (ATCC No. 23724) which had been manipulated by procedures known to those skilled in the art to also carry the Tn10 transposon. Kleckner, et al., *J. Mol Biol.* 116, 125 (1977). This lysate was used to infect *E. coli* C600 (lambda CI857) which contains an amber suppressor and a lambda prophage carrying the cI857 genotype. Lysates of tetracycline resistant colonies were prepared by heat induction by growing the tetracycline resistant colonies first in broth at 32° C. and thereafter at 42° C. for 90 minutes. The lysate was then plated on *E. coli* C600 and replica plated. The plaques appearing on *E. coli* C600 were replica plated at 32° C. on *E. coli* C600 and *E. coli* W3102 sup+ (lambda imm434) which contains the heteroimmune prophage lambda imm434. Kleckner N., et al., *Genetics* 90, 427 (1978). Plaques appearing on the heteroimmune strain are plated onto tetracycline plates. Plaques appearing on these plates are capable of transducing tetracycline resistance and are used in the above-described method for generating *E. coli* W3110 fhuA⁻.

Native t-PA and mutant t-PA were obtained from 10 liter cultures of these cells transformed with the appropriate t-PA mutant t-PA plasmid. Expression was induced by tryptophan deficient media.

6. Expression Vectors for t-PA Mutants in Mammalian Cells

Figure 9:
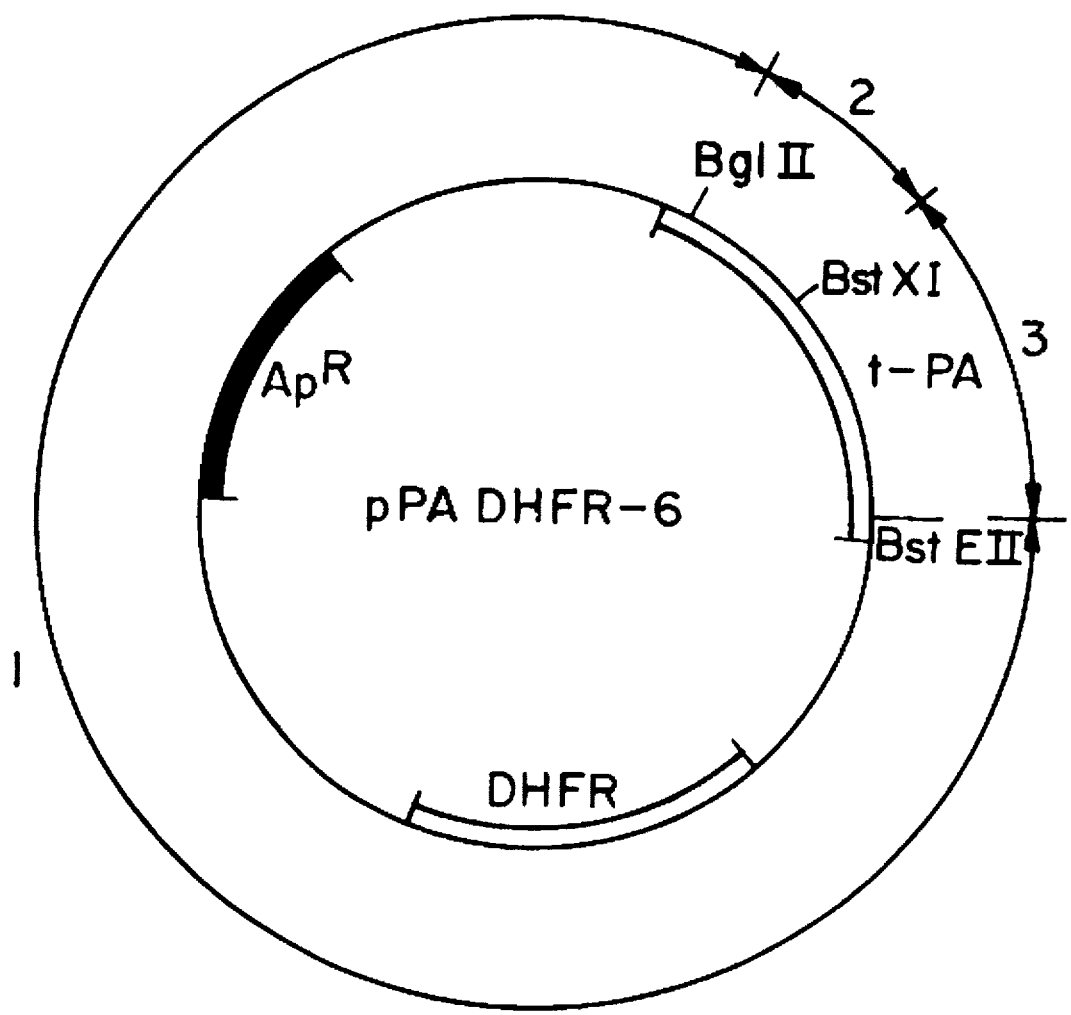
FIG. 9 depicts the plasmid pPADHFR-6 with relevant restriction sites.

The plasmid pPADHFR-6 (also designated pETPFR—see EPO Application Publication No. 93619 supra) is depicted in FIG. 9. The expression of the native t-PA structural gene is under the control of the early promoter for SV40 T-antigen. This promoter also controls the expression of the DHFR gene. Attention is directed to the BglII, BstXI and BstEII restriction sites. Vector fragment designated as fragment 1 in FIG. 9 was obtained by isolating the large fragment generated by digestion of pPADHFR-6 with BglII and BstEII. The fragment designated as fragment 2 in FIG. 9 was obtained by isolating the 400 base pair t-PA fragment obtained from the digestion of pPADHFR-6 with BglII and BstXI. A 1,141 base pair t-PA fragment containing the desired mutations and corresponding to fragment 3 in FIG. 9 was obtained by digesting RF DNA from each of the mutant t-PA clones with BstXI and GstEII. Fragments 1 and 2 were ligated with each fragment 3. The DNA mixtures were used to transform *E. coli*. From each of the transformants, the respective eukaryotic expression vectors were obtained:

pPADHFR-6 1B8
pPADHFR-6 2C9
pPADHFR-6 4A10
pPADHFR-6 3A7
pPADHFR-6 4B3

These plasmids, as well as the non-mutated t-PA expression vector pPADHFR-6, were used to transfect DHFR deficient CHO cells as disclosed supra.. (Graham, et al., *Virology* 52, 456 (1973); see also EPO Publication No. 093619) Native and mutant t-PA expression was amplified by exposing cultures to increasing concentrations of methotrexate.

For example, plasmids pPADHFR-6 2C9 and pPADHFR-6 1B8 were used to transfect DHRF deficient CHO cells (Urlab & Chasin (*PNAS* 77, 4216 (1980)) using the calcium phosphate precipitation method of Graham, et al., *Virology* 52, 46 (1973).

In each case, the colonies that arose in selective medium (medium lacking hypoxanthine, glycine, and thymidine (-HGT) were pooled and grown further in -HGT medium. These cells were plated at $2 \times 10^5$ cells per 100 mm plate in 20 nM methotrexate (MTX) to select for amplification of plasmid sequences. Five clones that grew in 250 nM MTX were extracted from the plate and all were found to be secreting t-PA into the medium. These clones were used for further study.

Preparation of Expression Vector

1. Plasmid pCISt-PA

Plasmid pCISt-PA was prepared as described, for example, in U.S. Ser. No. 07/071,506, filed 9 Jul. 1987, and U.S. Ser. No. 06/907,185, filed 12 Sep. 1986. In recapitulation, the vector pCIHt-PA containing the cytomegalovirus enhancer and promoter, the cytomegalovirus splice donor site and intron, the Ig variable region splice acceptor site, the cDNA-encoding t-PA (Pennica, et al., *Nature*, 301:214 (1983)) and the hepatitis surface antigen polyadenylation and transcription termination site was constructed first:

The vector pF8CIS containing the cytomegalovirus enhancer (Boshart, et al., *Cell*, 41:520 (1985)) and promoter (Thomsen, et al., *Proc. Natl. Acad. Sci.* (U.S.A.) 81:659 (1984)), the cytomegalovirus splice donor site and a portion of an intron (Sternberg, et al., *J. of Virol.*, 49:190 (1984)), the Ig variable region intron and splice acceptor site, the cDNA encoding factor VIII, and the SV40 polyadenylation site was constructed. The three parts of the construction are detailed below.

1. The ampicillin resistance marker and replication origin of the final vector was derived from the starting plasmid pUC13pML, a variant of the plasmid pML (Lusky, et al., *Nature*, 293:79 (1981)). pUC13pML was constructed by transferring the polylinker of pUC13 (Veira, et al., *Gene*, 19:259 (1982)) to the EcoRI and HindIII sites of pML. A second starting plasmid pUC8CMV was the source of the CMV enhancer, promoter and splice donor sequence. pUC8CMV was constructed by inserting nucleotides 1 through 732 for the CMV enhancer, promoter and splice donor sequence into the blunted PstI and SphI sites of pUC8—Veira, et al., supra. Synthetic BamHI-HindIII linkers (commercially available from New England Biolabs) were ligated to the cohesive BamHI end, creating a HindIII site. Following this ligation a HindIII-HincII digest was performed. This digest yielded a fragment of approximately 800 bp that contained the CMV enhancer, promoter and splice donor site. Following gel isolation, this 800-bp fragment was ligated to a 2900-bp piece of pUC13pML. The fragment required for the construction of pF18CIS was obtained by digestion of the above intermediate plasmid with SalI and HindIII. This 3123-bp piece contained the resistance marker for ampicillin, the origin of replication from pUC13pML, and the control sequences for the CMV, including the enhancer, promoter, and splice donor site.

2. The Ig variable region intron and splice acceptor sequence was constructed using a synthetic oligomer. A 99-mer and a 30-mer were chemically synthesized having the following sequence for the IgG intron and splice acceptor site (Bothwell, et al., *Cell*, 24:625 (1981)):

1 5'-AGTAGCAAGCTTGACGTGTGGCAGGCTTGA . .

31 GATCTGGCCATACACTTGAGTGACAATGA . . .

60 CATCCACTTTGCCTTTCTCTCCACAGGT . . .

88 GTCCACTCCCAG-3'

1 3'-CAGGTGAGGGTGCAGCTTGACGTCGTCGGA-5'

DNA polymerase I (Klenow fragment) filled in the synthetic piece and created a double-stranded fragment (Wartell, et al., *Gene*, 9:307 (1980)). This was followed by a double digest of PstI and HindIII. This synthetic linker was cloned into pUC13 (Veira, et al., supra) at the PstI and HindIII sites. The clone containing the synthetic oligonucleotide, labeled pUCIg.10, was digested with PstI. A ClaI site was added to this fragment by use of a PstI-ClaI linker. Following digestion with HindIII a 118- bp piece containing part of the Ig intron and the Ig variable region splice acceptor was gel isolated.

3. The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described in Veira, et al., supra. pUC.SV40 was then digested with EcoRI and HpaI. A 143-bp fragment containing only the SV40 polyadenylation site was gel isolated from this digest. Two additional fragments were gel isolated following digestion of pSVE.8c1D (EPO Pub. No. 160,457). The 4.8-kb fragment generated by EcoRI and ClaI digest contains the SV40-DHFR transcription unit, the origin of replication of pML, and the ampicillin resistance marker. The 7.5-kb fragment produced following digestion with ClaI and HpaI contains the cDNA for Factor VIII. A three-part ligation yields pSVE.8c24D. This intermediate plasmid was digested by ClaI and SalI to give a 9611-bp fragment containing the cDNA for Factor VIII with the SV40 polyadenylation and transcription termination sites followed by the SV40 DHFR transcription unit.

The final three-part ligation to yield pF8CIS used: a) the 3123-bp SalI-HindIII fragment containing the origin of replication, the ampicillin resistance marker and the CMV enhancer, promoter and splice donor; b) the 118-bp HindIII-ClaI fragment containing the Ig intron and splice acceptor; and c) a 9611-bp ClaI-SalI fragment containing the cDNA for Factor VIII, SV40 polyadenylation site, and the SV40 DHFR transcription unit.

Next, the completion of the construction of plasmid pCIHt-PA from intermediate plasmid pCIa t-PA and plasmid pF8CIS (above) was undertaken:

The t-PA cDNA was first cloned into pML to provide a ClaI site at the 5' end of the gene. To do this, a 3238-bp HindIII fragment from pSVpa-DHFR (otherwise referred to as pETPFR, supra) was inserted into the HindIII site of pML (Lusky, et al., supra). Colonies were screened for clones that have the 5' end of the cDNA juxtaposed to the ClaI site. The intermediate plasmid was labeled pCLAt-PA. A t-PA cDNA followed by the 3'- polyadenylation regions was isolated as a ClaI-KpnI fragment of 2870 bp. This fragment was ligated to the 5146-bp fragment of pF8CIS. This ClaI-KpnI fragment of the CIS vector provided the 5' control region, a SV40-DHFR transcriptional unit, the ampicillin resistance gene, and the origin region from pML.

Expression levels of t-PA were obtained by transfecting CHO or 293 cells with pCIHt-PA, in accordance with methods generally known per se and described supra. Media from the transfected 293 cells, for example, were assayed, demonstrating that pCIHt-PA produced 420 ng/ml of t-PA.

The vector pCISt-PA containing the cytomegalovirus enhancer and promoter, the cytomegalovirus splice donor site and intron, the Ig variable region splice acceptor site, the cDNA encoding t-PA, and the pSV40 polyadenylation sequence was finally constructed as follows:

The starting vectors for this construction were pCIHt-PA and pF8CIS (supra). The latter vector has the same 5' controls as pCIHt-PA, but includes the cDNA for Factor VIII and the SV40 polyadenylation site. SacII was used to cleave 3' of the t-PA cDNA. The resultant 3' overhang was blunted by T4 polymerase. pCIHt-PA was then cut with ClaI. This site separates the chimeric intron cleaving between the CMV intronic sequences and the Ig variable region intron. An 2870-bp fragment was gel isolated from the ClaI treatment. The SV40 polyadenylation site, DHFR, transcription control, bacterial origin of replication, and amp' gene, as well as the CMV enhancer and promoter and splice donor were isolated from pF8CIS. These elements were isolated into fragments as a 2525-bp Sal-BamHI fragment and a HpaI-Sal and 3113-bp fragment. A three-part ligation of the KpnI (blunt)-ClaI fragment with the HpaI-Sal fragment and Sal to BamHI fragment yields pCISt-PA, which was expressed in both CHO and 293 cells as discussed above for plasmid pCIHt-PA, giving 55 and 3000 ng/ml of t-PA, respectively.

Oligonucleotide Design

Several 23-mer oligonucleotides having the following sequences 5'-G-CCT-CAG-TTT-XYZ-ATC-AAA-GGA-G-3' where XYZ is, respectively,

| | |
|---|---|
| GCC (ala) A** | ATG (met) M |
| TGC (cys) C | AAC (asn) N |
| GAC (asp) D | CAG (gln) Q |
| TTC (phe) F | AGC (ser) S |
| CAC (his) H | AAC (thr) T |
| AAG (lys) K | GTG (val) V |
| CTG (leu) L | TGC (trp) W |
| | TAC (tyr) Y |

**Single letter alphabet of amino acids (supra.)

were synthesized as above by the phosphotriester method of Crea, et al., *Nucleic Acids Research* 8, 2331 (1980).

Construction of Recombinant M13 Template

Figure 13:
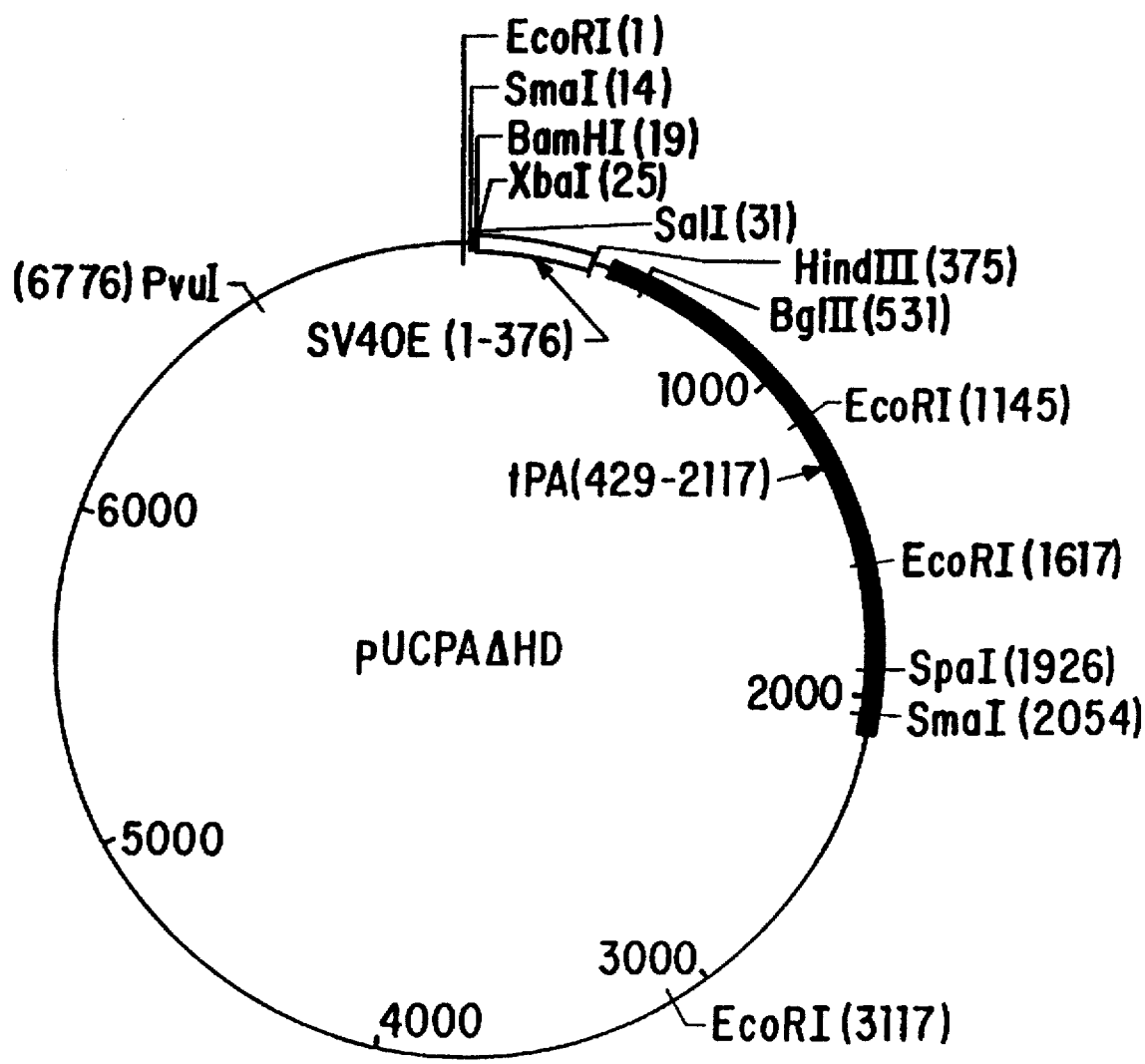
FIG. 13 depicts a restriction map of a starting plasmid pUCPAΔHD.
Figure 14:
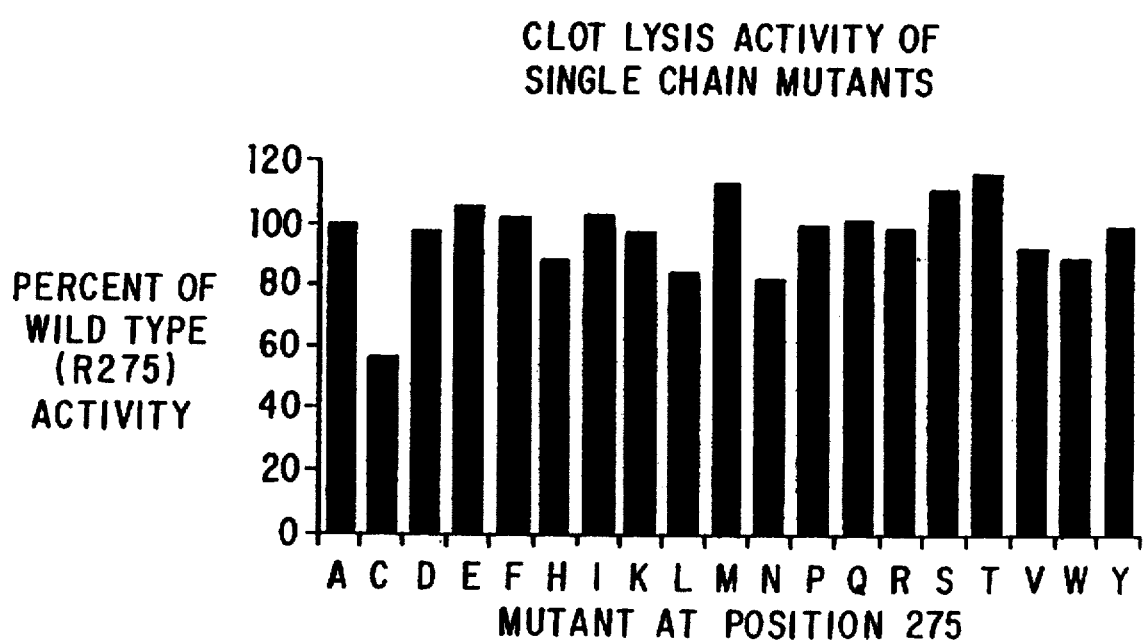
FIG. 14 is a graphic display of specific activities of various 275 mutants hereof in an in vitro clot lysis assay (ELISA used to determine protein concentration).
Figure 15:
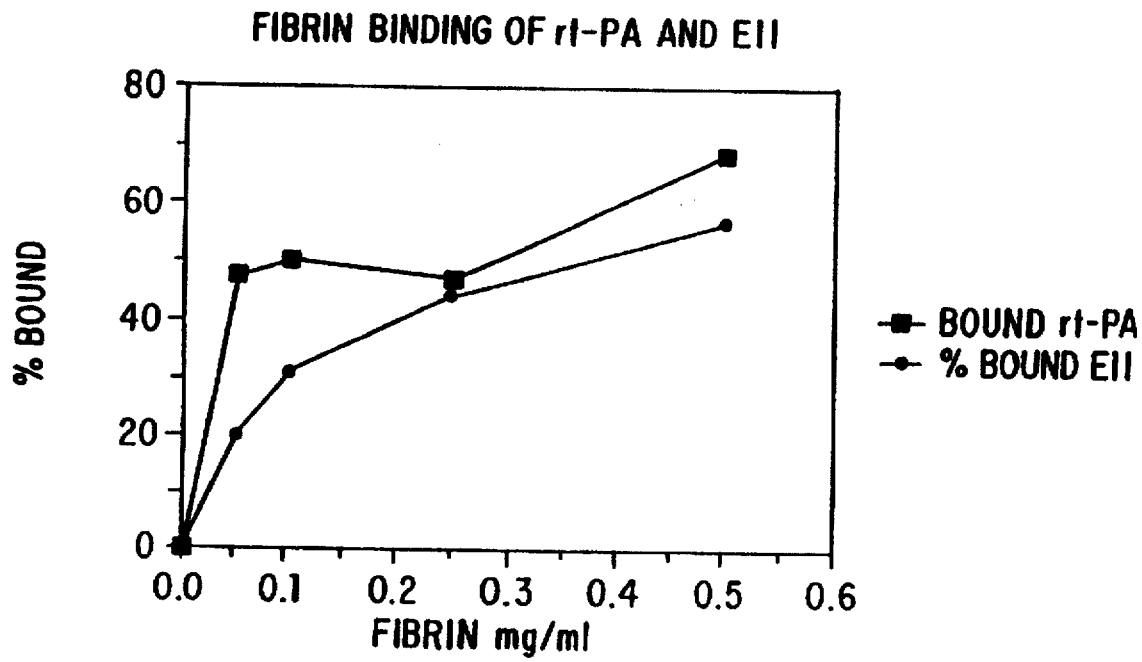
FIG. 15 is a graphic display of fibrin binding activity of E275I277 t-PA ("EII") versus wild-type t-PA ("rt-PA").
Figure 16:
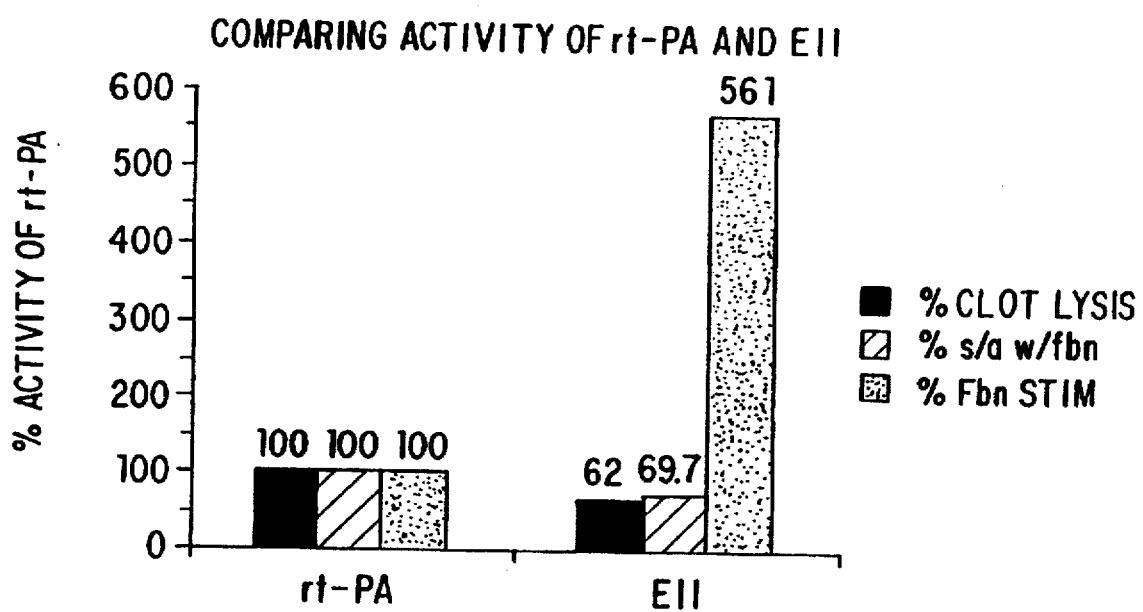
FIG. 16 is a graphic display comparing the activities of E275I277 t-PA ("EII") and wild-type t-PA ("rt-PA").

Plasmid pUCPAΔHD (FIG. 13) is a derivative of plasmid designated pETPFR (otherwise designated pPADHFR-6 disclosed in European Application No. 93619, supra), with the following modifications: 1) 166 bp of 5' untranslated DNA has been trimmed from the 5' end of the t-PA gene, using exonuclease Bal 31; 2) a Hind III site has been added to the new 5' end of the t-PA gene; 3) a polylinker, containing recognition sites for EcoRI, SacI, SmaI, BamHI, BaI, Sal I, and Pvu II, has been added to the 5' end of the SV40 early promoter that drives t-PA expression; 4) the Hind III site at position 3539 of pETPFR has been destroyed by a Klenow fill-in reaction.

Plasmid pUCPAΔHD (FIG. 13) was digested with SmaI, and the ca. 2.0 kb fragment containing the t-PA gene through codon No. 507 was isolated by PAGE and electroelution of the fragment from the gel. M13mp10 (Messing, *Methods in Enzymology* 101, 20 (1983)) vector was also digested with SmaI extracted once with phenol, chloroform, ethanol precipitated, and re-suspended in 50 MMtris pH 8.0, 1 mMEDIA (TE). The ca. 2.0 kb fragment from pUCPAΔHD was ligated into the SmaI cut M13mp10 using T4 DNA ligase and the resulting DNA was used to transform *E. coli* JM101. The resulting phage was isolated and the presence of the insert was verified and its orientation determined by restriction analysis of phage minipreps. One recombinant phage, M13/t-PA-SMA, was chosen as template for subsequent mutagenesis.

Mutagenesis Reaction

The several oligonucleotides (23-mers) prepared as described above were separately annealed to single-stranded M13/t-PA-SMA DNA, and treated with *E. coli* DNA polymerase Klenow fragment in the presence of dNTPs and T4 DNA ligase to create in vitro heteroduplex RF molecules, as described by Adelman, et al., *DNA* 2, 183 (1983). These molecules were used to transform strain JM101 (ATCC No. 33876) and phage incorporating the desired mutation were detected by plague hybridization using the mutagenesis primer as a probe. (Adelman, et al., *DNA* 2, 183 (1983). Mutant phage were isolated and contained the respective (XYZ) mutant DNA at position 275.

Subcloning the (XYZ) Mutants into Expression Plasmid pCistPA

Double stranded DNA of the respective (XYZ) mutants described above, above were digested with ScaI and ApaI and the fragments purified by PAGE. These fragments were then used in a three way ScaI-ApaI, SacII-ScaI ligation into pCistPA to replace the corresponding fragment in pCistPA.

Recombinant plasmids containing the t-PA gene fragment were identified and introduced into and expressed in human embryonic kidney (293) cells (Graham, et al., *J. Gen. Virol.* 36, 59 (1977)) using generally available methods.

The t-PA mutants are obtained from the resulting cell line and are separated for use, preferably using a t-PA specific polyclonal antibody purification column.

Variant t-PA and t-PA Purification

The various t-PAs expressed in mammalian cells as described above were secreted into the cell culture medium. The medium containing such t-PAs was used directly in various assays to be described hereafter or was subjected to one or more of the following purification steps to increase the purity of t-PA or mutant t-PA prior to such assays.

Media from CHO cells containing mutant t-PA was batch extracted with chelating Sepharose (Pharmacia) (10–20 mL resin/L media) activated with zinc chloride as described by Rijken, et al., *Biochim. & Biophys. Acta.* 580 140 (1979) and collected on a filter. The resin was poured into a column, washed with a buffer containing 0.02M sodium phosphate, pH 8.0, 0.25M NaCl, 0.01 percent TWEEN 80 and 10 mg/liter aprotinin. The t-PA was eluted with the same buffer containing 50 mM imidazole. The t-PA pool was dialyzed into 0.02M sodium phosphate, pH 8, 0.25M NaCl and 0.01 percent TWEEN 80 and loaded onto a lysine Sepharose resin, Radcliffe, et al., *Arch. Biochem. Biophys.* 189, 185 (1978) and Allen, et al., *Thrombosis Heamostasis* 45, 43 (1981), or benzamidine Sepharose resin, Bykowska, et al., *Biochim. & Biophys. Acta,* 703, 113 (1982). The lysine-sepharose column was washed briefly with 0.02M sodium phosphate, pH 8, 1M NaCl and 0.01 percent TWEEN 80 and t-PA or mutant t-PA eluted with the same buffer containing 0.5M arginine. The benzamidine Sepharose was washed with the dialysis buffer and eluted with the dialysis buffer containing 1M guanidine. The resulting proteins were greater than 90% pure as analyzed by SDS-PAGE. In addition to the use of the foregoing purification techniques, a t-PA specific immobilized polyclonal antibody or immobilized monoclonal antibody column may be used (see, for example, Nielsen, et al., *EMBO J.* 2, 115 (1983).

SDS Polyacrylamide Gel Electrophoresis (SDS-PAGE)

Samples of media containing t-PA protein or the t-PA mutant proteins were concentrated by vacuum and diluted into sodium dodecyl sulfate (SDS) sample buffer. Where indicated, 10 mM dithiothreitol (DTT) was added to reduce the protein disulfides. Discontinuous SDS electrophoresis using 10% or 7 to 17% polyacrylamide resolving gels was performed according to the procedure of Laemmli. [Laemmli, et al., *Nature* 227, 680 (1970)]. For analysis of plasma samples, 4% to 10% SDS polyacrylamide gradient resolving gels were used with the buffer system of Laemmli. Estimated molecular weights (Mr) from SDS-PAGE analysis were obtained by comparison to the mobility of protein of known molecular weight.

Assay Methods

Bubble Release Clot Lysis

Recombinant (non-variant) t-PA and variant t-PAs hereof (variant t-PA) were assayed for their ability to solubilize fibrin clots by the bubble release clot lysis assay.

Briefly, thrombin (Sigma Chemical Co.) was dissolved in distilled water to approximately 1000 units/ml. This stock solution was diluted 1:30 with assay buffer which contained 0.06M monobasic sodium phosphate, 0.06M dibasic sodium phosphate, 200 mg/liter sodium azide and 0.01% TWEEN 80. A series of test tubes containing 0.5 ml of diluted thrombin (30–40 units/ml) and 0.5 ml of either various concentrations of t-PA (16 ng/ml to $1 \times 10^6$ ng/ml); appropriate controls or unknown sample in appropriate dilutions were prepared. A second series of test tubes containing 20 µl plasminogen (1.0 mg/ml), and 1.0 ml of fibrinogen (1 mg/ml) and 10 µl of hollow glass microspheres greater than 45 mesh (3M Company) was also prepared.

The above reagents and test tubes were kept on ice until the final step of the assay. 200 µl of either the thrombin-t-PA or thrombin-mutant t-PA solutions were added sequentially to a test tube containing the plasminogen, fibrinogen, and microspheres, vortexed for 15 seconds and placed in a 37° C. water bath. Clots formed in each tube within 30 seconds. The time between t-PA addition and the endpoint of the reaction was measured. The endpoint was defined as the time when the microspheres in the assay had risen to the surface.

The amount of thrombolytic activity of a particular sample was determined by reference to s standard t-PA curve. Specific activity was calculated based on the amount of t-PA or mutant t-PA present as determined by radioimmunoassay.

In Vitro Clot Lysis Assay

Recombinant t-PA and variant t-PA were also assayed in an in vitro clot lysis system.

Briefly, human blood was collected with 3.13% sodium citrate as anticoagulant and the cellular fraction removed by centrifugation. 50 µl of 0.5M $CaCl_2$ 25 µl bovine-thrombin (100 units/ml) and 10 µl of human $^{125}I$- fibrinogen (100,000 cpm/10 µl) was added to each ml of plasma. This plasma mix was aspirated into silicon tubing with an inside diameter of 4 mm and incubated at 37° C. for 1 hour. Segments (1 cm) of the tubing were cut and the clot removed. The clots were placed in buffer consisting of 0.3M NaCl, 0.02M sodium citrate, pH 5, and 0.01% TWEEN 80. The clots were rinsed four times in one hour with fresh buffer. The amount of radioactivity in the last rinse did not exceed about 10% of the amount of radioactivity in the clot. Each clot was placed in 2.5 ml of plasma. A 250 µl sample of plasma was taken as a zero point. A sample of t-PA or mutant t-PA was added in a volume of 100 µl. Samples (250 HI) were taken at 1, 2, 3 and 4 hours and the radioactivity contained therein determined. Standards containing 5, 10, 20 and 40 units of t-PA activity per ml were run in parallel. The percent lysis was calculated after correction for volume changes after each sample.

Chromogenic Assays

S-2288: t-PA may be measured directly using the Kabi synthetic tripeptide chromogenic substrate, S-2288 (Helena Laboratories, Beaumont, Tex.). For this assay, t-PA and 1 mM S-2288 (final concentration) in 0.05M Tris, pH 7.4 containing 0.012M NaCl and 0.01 percent TWEEN 80 were incubated at 37° C. for 10 minutes. The reaction was stopped by the addition of 50 µl of glacial acetic acid to 0.5 ml reaction mixture. The activity was calculated from the absorbance at 405 nm using the following equation, standardized by the manufacturer:

$$\text{Activity in 0.5 ml reaction mixture (IU, international units)} = \frac{\Delta OD \times 793.65 \ OD}{\text{time of incubation}} \ \text{IU-min}$$

S-2251: Plasminogen activation by t-PA was measured using the Kabi specific tripeptide chromogenic substrate specific for plasmin, S-2251 (Helena Laboratories). An aliquot of the sample was mixed with 0.10 ml of 0.7 mg/ml plasminogen (0.05M Tris, pH 7.4 containing 0.012 m NaCl) plus 0.02 ml of human fibrinogen 20 mgs/ml (0.05M Tris HCl, pH 7.4, containing 0.012M NaCl) and the volume adjusted to 0.15 ml. The mixture was incubated at 37° C. for 10 minutes. 0.35 ml of S2251 (0.86 mM solution in above buffer) was added, and the reaction continued for 5 or 10 minutes at 37° C. Glacial acetic acid (50 µl) was added to terminate the reaction and the absorbance at 405 nm was measured. Quantitation of the amount of activity was obtained by comparison to the results obtained using a recombinant native t-PA sample which had been standardized using the S-2288 assay. This was necessary initially because the absorbance at 405 nm varied from day to day as the plasminogen aged and also changed if different preparations of plasminogen and fibrinogen were used. This variability was ultimately reduced by careful preparation of large amounts of human plasminogen (gluplasminogen) with subsequent lyophilization of aliquots of the material. The aliquots were stored at −20° C. Prior to use, the redissolved plasminogen preparations were stored at ODC for not more than 4 hours. Stimulation of t-PA activity by fibrinogen was measured by comparing the activity of solutions containing high concentrations of fibrinogen to similar reaction mixtures in which fibrinogen had been omitted. Due to the insolubility of fibrin, fibrinogen was used in this assay. The stimulation by high concentrations of fibrinogen appears to mimic the stimulation that would be expected by the insoluble fibrin.

In vivo Inhibitor-Complex Assay

Recombinant t-PA and variant t-PAs were assayed in vitro to determine their reactivity with naturally occurring inhibitors of t-PA activity. Generally, t-PA and variant t-PA were iodinated with $^{125}I$ by using Iodobeads (Pierce Chemical Co.) resulting in t-PA or mutant t-PA having specific radioactivities approximately $2 \times 10^6$ cpm/µg. For in vitro complex formation, the radiolabeled t-PA (1 µg) was added to freshly drawn citrated human whole blood (500 µl). The samples were incubated at room temperature and the reaction stopped by dilution of an aliquot into 2% SDS. Samples were analyzed in 4 to 10% polyacrylamide gradient SDS-PAGE. Complexes were detected by autoradiography.

Fibrin Binding Assay

Figure 11:
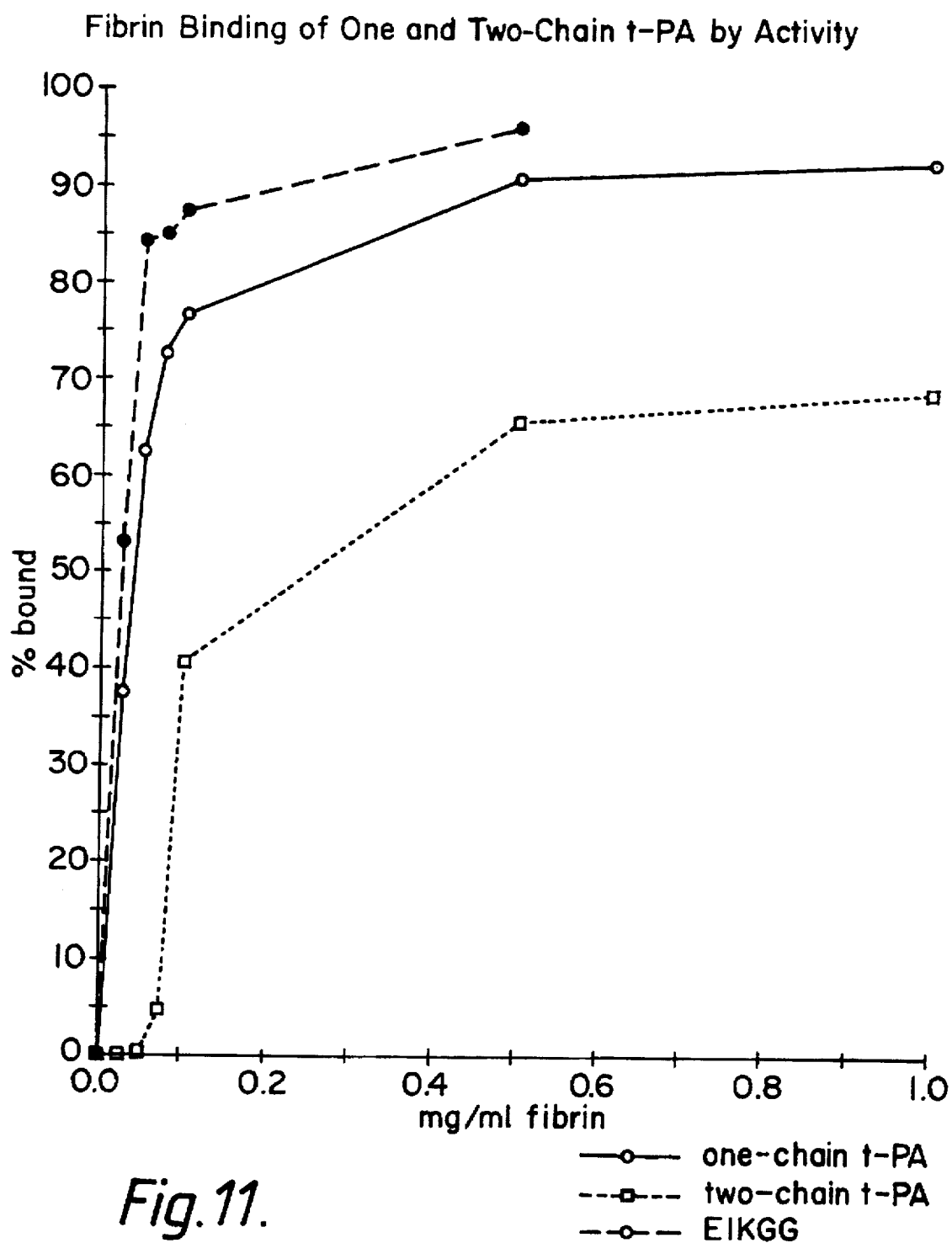
FIG. 11 shows the fibrin binding properties of one-chain t-PA, two-chain t-PA and of the mutated one-chain t-PA (EIKCC).

The method for fibrin binding is a modification of the method described by Rijken, et al., *J. Biol. Chem.* 257, 2920 (1982). The t-PA sample to be tested (500 ng) is added to a solution containing 0.05M Tris, pH 7.4, 0.12M NaCl, 0.01% TWEEN 80, 1 mg/ml human serum albumin, and various concentrations of plasminogen free fibrinogen (0, 0.025, 0.05, 0.075, 0.1, 0.5 and 1.0 m/ml). The final volume of the reaction mixture is 1 ml. The sample is incubated at 37° C. for five minutes, followed by the addition of 1 unit of thrombin. The samples are incubated for one hour at 37° C. The clot is removed using a glass rod, and the amount of t-PA remaining unbound in the supernatant is determined. The data is plotted as percent t-PA bound versus the fibrinogen concentration (FIG. 11).

In Vivo Clot Lysis

The in vivo clot lysis model of Collen, et al., *J. Clin. Invest.* 71, 368 (1983), was used. Male New Zealand white rabbits between 2.5 and 3 kg were anesthetized with ketamine, the jugular vein was catheterized and small communicating vessels in the region were ligated. Approximately 2 cm of the jugular was isolated with reversible ligatures, a thread was passed from the proximal to the distal end of the segment, the segment was flushed with a saline thrombin solution and filled with fresh rabbit blood which contained $^{125}I$ human fibrinogen. After 30 minutes blood flow was resumed across the clot. The t-PA i.v. infusion was started with an initial bolus of 10% of the total dose. The infusion was delivered over 4 hours. Thirty minutes after the end of the infusion the clot was harvested and counted. The recovery of radioactivity was used as a quality control; blood samples, urine, swabs and syringes were counted to assure that the estimate of the mount of radioactivity present in the initial clot was accurate.

Assay Results t-PA mutants with the following sequences at the two-chain activation site, residues 270 through 279, have been expressed in both *E. coli* and Chinese Hamster Ovary cells (CHO cells):

| | 275 | | | 279 | | | |
|---|---|---|---|---|---|---|---|
| Native | —Arg—Ile—Lys—Gly—Gly— | | | | | (RIKGG) | (t-PA) |
| 1B8 | —Gly—Ile—Lys—Gly—Gly— | | | | | (GIKGG) | (G275 t-PA) |
| 2C9 | —Glu—Ile—Lys—Gly—Gly— | | | | | (EIKGG) | (E275 t-PA) |

Western Blots and Zymography

The EIKGG & GIKGG mutants expressed in CHO cells were analyzed by Western blots derived from reduced and non-reduced SDS-PAGE gels. Native single-chain t-PA shows up as two bands having molecular weights of 52,000 and 50,000 daltons due to a difference in the extent of glycosylation. The EIKGG mutant from a non reduced SDS-PAGE showed one major immunoreactive band at a molecular weight of approximately 50,000 daltons. The Western blot of the mutant GIKGG from a non-reduced SDS-PAGE, however, showed a molecular weight of 55,000 daltons. The difference in apparent molecular weight of the GIKGC mutant as compared to native t-PA may indicate a slightly different conformation or carbohydrate structure compared to native t-PA, perhaps attributable to a conformational aberration due to a presumed presence of a second, adventitious mutation at amino acid 261 (cys to tyr). Cleavage of the protein at arg 275 can be detected by a lower molecular weight of t-PA when analyzed following reduction (thereby separating the protease and Kringle chains). Zymographs of the reduced SDS-PAGE gels showed that plasminogen activator activity in these samples was at the molecular weight of the immunoreactive band of the single-chain form of t-PA (approximately 60,000). The two-chain form of t-PA has an electrophoretic mobility consistent with a molecular weight of approximately 30,000 daltons. The other 275 (XYZ) mutants prepared as described above appear as single bands when subjected to both reduced and unreduced SDS-PAGE, except $Lys_{275}$ which showed a lower molecular weight band following reduction. This procedure demonstrated that single-chain forms of the mutant t-PA proteins, with the single exception, were present in the media from transformed cells.

S-2251 Assay

Analysis of the native and a variant EIKGG t-PA by the S-2251 assay is shown in Table I. These values were obtained prior to the use of glu-plasminogen in the assay in order to decrease assay variability. The naturally occurring t-PA sequence RIKGG was assigned an arbitrary specific activity in the presence of fibrinogen on the basis of the S2288 assay. This standard t-PA was assayed with each of the EIKGG t-PA variants to normalize results.

As can be seen the EIKGG t-PA variant, regardless of the degree of purification, has a specific activity in the S2251 plus fibrinogen assay greater than that for the recombinant t-PA.

TABLE I

| Mutation | Variant | S-2251 + Fibrinogen | S-2251 − Fibrinogen | Fibrinogen Stimulation |
|---|---|---|---|---|
| RIKGG[1] | native | 250,000[4] | 25,000 | 10.0 |
| EIKGG[1] | 2C9 | 1,000,000 | 3,400 | 290.0 |
| EIKGG[2] | 2C9 | 420,000 | 3,100 | 134.0 |
| EIKGG[3] | 2C9 | 520,000 | 7,000 | 74.0 |

[1]purified using zinc chelate lysine-agarose
[2]purified using zinc chelate and benamidine agarose
[3]assayed with no purification
[4]assigned activity The data in Table IA were obtained using high quality, lyophilized, glu-plasminogen. With a more reproducible assay, the EIKGG mutant was found to be equal in activity in the S-2251 assay in the presence of fibrinogen. In the absence of fibrinogen, the mutant was still less active than native (Tables I and IA), demonstrating a greater specificity.

TABLE IA

| Mutation | Variant | S-2251 + Fibrinogen | S-2251 − Fibrinogen | Fibrinogen Stimulation |
|---|---|---|---|---|
| RIKGG[1] | native | 250,000[2] | 17,600 | 14 |
| EIKGG[1] | 2C9 | 248,000 | 500 | 500 |

[1]purified using zinc chelate lysine-agarose
[2]assigned activity

The other 275 (XYZ) mutants prepared as described above were tested and found to exhibit activity comparable to the EIK mutant.

Bubble Release Clot Lysis and In Vitro Clot Lysis Assay

The bubble release clot lysis assay was used to determine the specific activity of recombinant t-PA and the purified EIKGG t-PA variant. The activity of each of these t-PAs was determined by the procedures described above. The concentration of t-PA and EIKGG variant t-PA was determined by radioimmunoassay. The results of this assay including specific activity are shown in Table II.

TABLE II

| Sample | I.D. | U/ml Activity | Protein Conc. mg/ml | Specific Activity |
|---|---|---|---|---|
| 1 | EIKGG* | 8440 | 0.088 | 95,909 |
| 2 | EIKGG* | 7698 | 0.088 | 87,477 |
| 3 | t-PA** | 5640 | 0.088 | 64,090 |

1) Frozen - thawed once
2) Frozen - thawed four times
*purified using zinc-chelate and benzamidine-agarose
**purified using zinc chelate and lysine-agarose The bubble release clot lysis assay demonstrates that a one-chain variant of t-PA, specifically the EIKGG variant t-PA, has a specific activity 50% greater than recombinant t-PA. As can be seen repeated freezing and thawing resulted in a slight decrease in the specific activity of the EIKGG t-PA variant. However, the variant t-PA still maintained a specific activity greater than that of the recombinant t-PA.

Within the limits of assay reproducibility, and using more refined techniques (See Carlson, et al., Anal. Biochem. 168, 428 (1988)), the other 275 (XYZ) mutants demonstrated clot lysis activity comparable to the EIK mutant, with the exception of CIK ($C_{275}$ t-PA) which showed a lower activity. In this assay, EIK (E275 t-PA) was about equivalent to wild-type (RIK) t-PA.

In Vivo Inhibitor-Complex Assay

Figure 10:
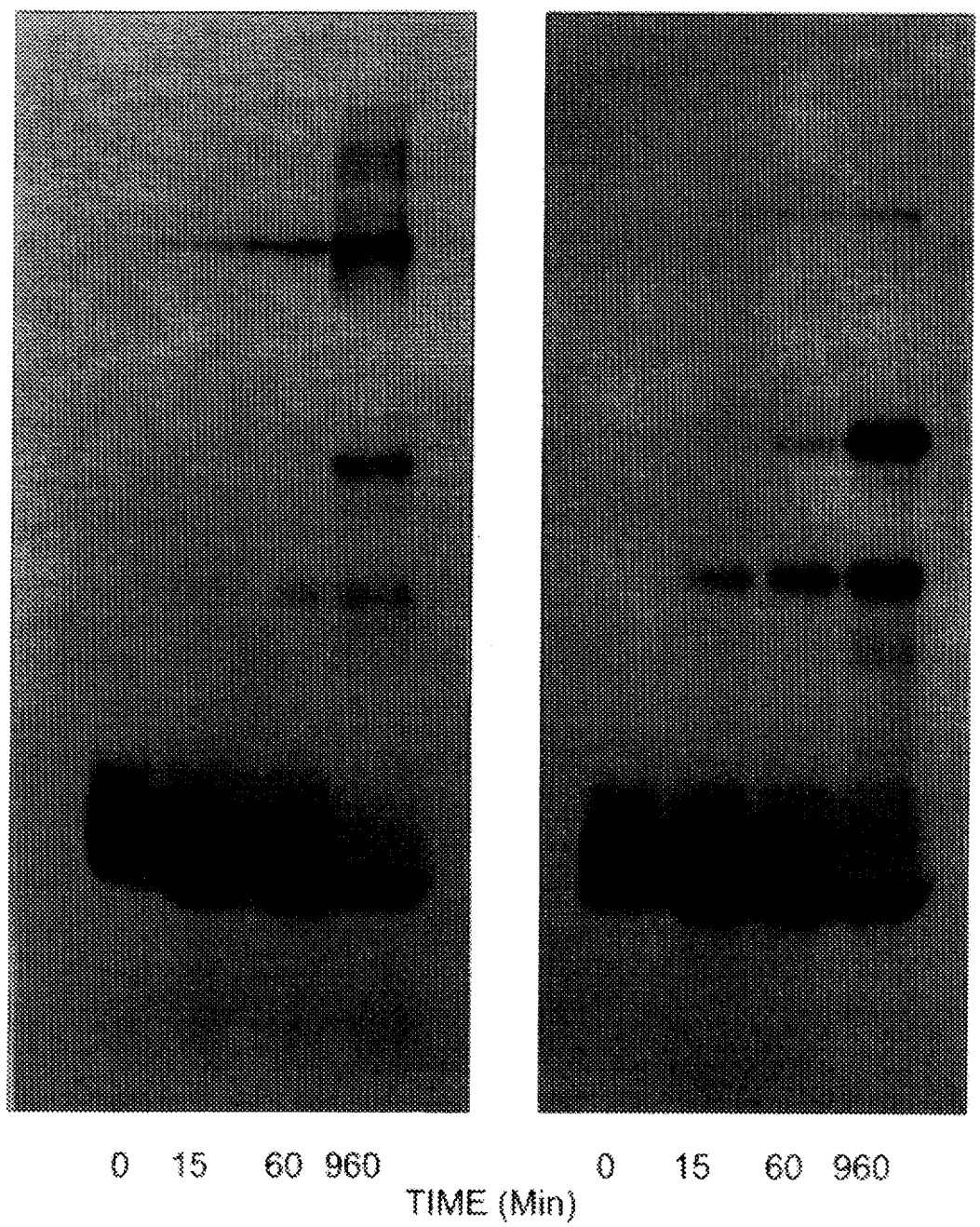
FIG. 10 depicts the plasma protease inhibitor complexes formed by radiolabeled t-PA (left panel) and EIKCC t-PA (right panel) as by autoradiography of an SDS-PAGE gel.

The inactivation of proteases by plasma protease inhibitors is a well-studied mechanism for inactivating serum proteases. The resulting complexes are stable to denaturation and can be assessed by electrophoresis on SDS-PAGE. In this procedure, radiolabeled t-PA is added to plasma or whole blood and the sample incubated at 37° C. The sample is subjected to SDS-PAGE followed by autoradiography. The detection of radiolabel at positions of Mr greater than free t-PA is an indication of the amount of t-PA protease inhibitor complex which has been formed. When analyzed in rat blood, t-PA was found to slowly form complexes with Mr greater than 200,000. After several hours of incubation, greater than 70% of the radiolabel could be detected in such complexes. In contrast, the mutated t-PA did not form these complexes; the bulk of the radiolabel detected by autoradiography remained at the position of free, uninactivated enzyme. When a similar analysis was performed in human blood, (FIG. 10) t-PA also formed such complexes, but in addition formed complexes of Mr between 100,000 and 200,000. As with the rat blood, the mutant t-PA formed markedly less inhibitor complexes with Mr greater than 200,000. The protease inhibitor complexes with Mr values between 100,000 and 200,000 were still present. These results indicate that the mutant is not inactivated by the proteinase inhibitor(s) which form complexes with Mr values greater than 200,000. Species differences are noted in the reactivity of both t-PA and the mutated t-PA in the formation of complexes between 100,000 and 200,000.

Fibrin Binding

It has previously been reported that one-chain and two-chain forms of t-PA have approximately equal affinity for fibrin (Rijken, et al., J. Biol. Chem. 257, 2920 (1982). In the assay described herein, in contrast, a markedly higher affinity for fibrin was observed for the one-chain form of t-PA as compared to the two-chain form (FIG. 11).

All of the other 275 (XYZ) mutants had activities comparable to EIK in the fibrin binding assay. It was determined that the GIK (G275 t-PA) mutant, prepared as described above, exhibited lower specific activity in this assay compared with RIK, thought to be attributable to a conformational aberration due to presumed presence of a second, adventitious mutation at amino acid 261 (cys to tyr). The CIK and KIK mutants also displayed lower, than wild-type (RIK), activities thought due respectively to some misfolding and some 2-chain form present.

In Vivo Clot Lysis

Figure 12:
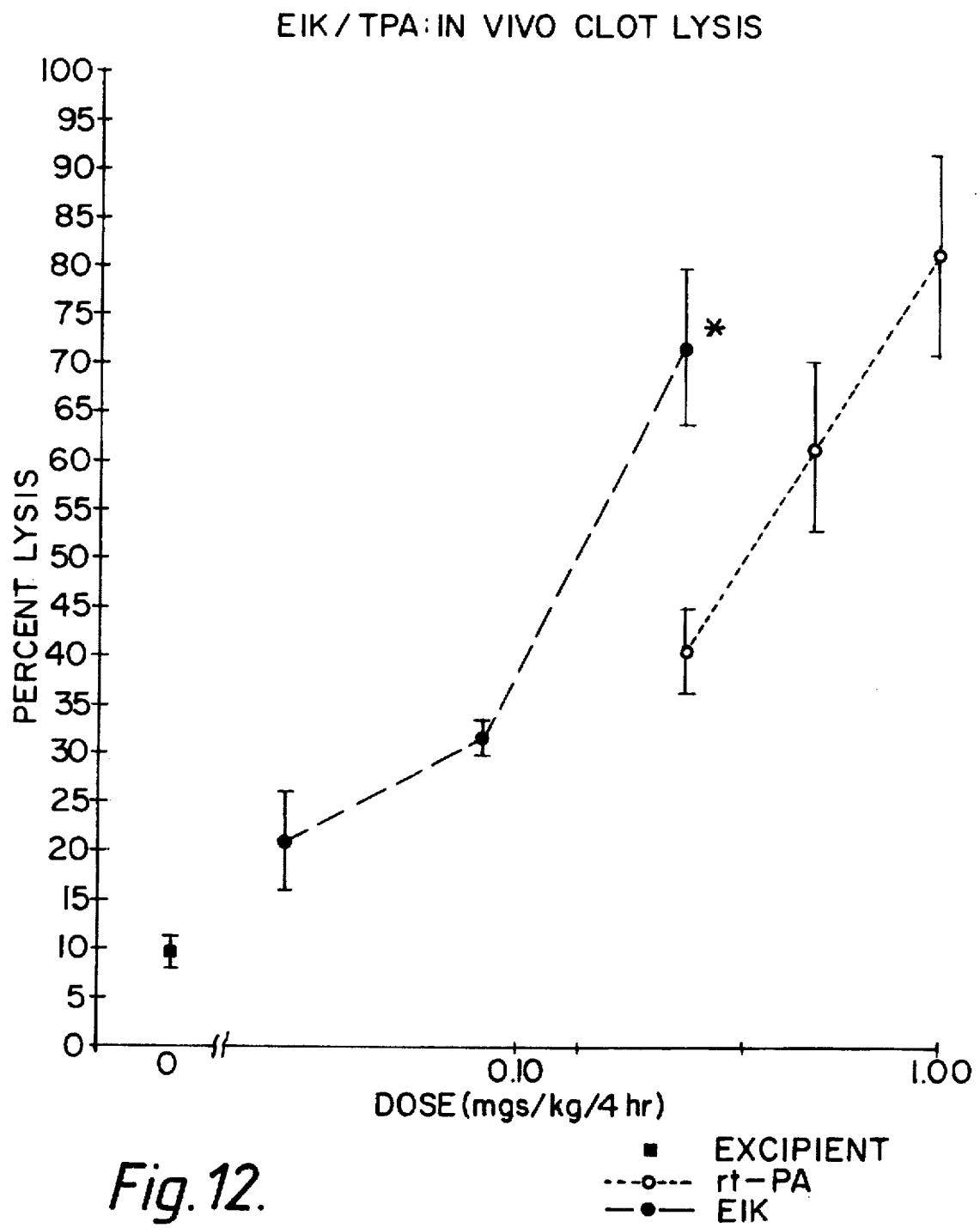
FIG. 12 depicts a dose-response curve of clot lysis (EIK is mutated one-chain t-PA; rt-PA is non-mutated t-PA).

FIG. 12 shows the relative dose response curves for t-PA (o) and the EIK mutant (o). The data are presented as the Mean +/-SEM with 5 rabbits in each group. The distance between the two curves at the 50% lysis point was measured and the potency of the EIK form of t-PA was estimated to be 2.4 times greater than the non-mutated form (RIK). A statistically significant difference was achieved at the 0.25 mg/kg dose (p<0.01).

EXAMPLE 2

These variants have amino acid substitutions or deletions at positions 274–277. The resulting variants may or may not be resistant to hydrolysis by plasmin, but all show enhanced fibrin specificity compared to wild-type t-PA.

1. Construction of pRK7-t-PA

Plasmid pRK7 was used as the vector for generation of the t-PA mutants. pRK7 is identical to pRK5 (EP Pub. No. 307,247 published Mar. 15, 1989), except that the order of the endonuclease restriction sites in the polylinker region between ClaI and HindIII is reversed. The t-PA cDNA (Pennica et al., Nature, 301:214 (1983)) was prepared for insertion into the vector by cutting with restriction endonuclease HindIII (which cuts 49 base pairs 5' of the ATG start codon) and restriction endonuclease BalI (which cuts 276 base pairs downstream of the TGA stop codon). This cDNA was ligated into pRK7 previously cut with HindIII and SmaI using standard ligation methodology (Maniatis et al., Molecular Cloning: A Laboratory Manual, Cold Spring Harbor Laboratory, New York, 1982). This construct was named pRK7-t-PA.

2. Site-directed Mutagenesis of pRK7-t-PA

Site-directed mutagenesis of t-PA cDNA was performed by the method of Taylor et al., Nucl. Acids. Res., 13:8765 (1985) using a kit purchased from the Amersham Corporation (catalog number RPN 1253). For generation of the desired mutants, oligonucleotides of sequences coding for the desired amino acid substitutions were synthesized and used as primers. These oligonucleotides were annealed to single-stranded pRK7-t-PA that had been prepared by standard procedures (Viera et al., Meth. Enz., 143:3 (1987)).

A mixture of three deoxyribonucleotides, deoxyriboadenosine (dATP), deoxyriboguanosine (dGTP), and deoxyribothymidine (dTTP), was combined with a modified thiodeoxyribocytosine called dCTP(aS) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the mutated bases was generated. In addition, this new strand of DNA contained dCTP(aS) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

The following oligonucleotides were prepared to use as primers to generate pRK7-t-PA molecules:

| Variant* | Oligo Number | Sequence |
|---|---|---|
| Des 275–277 | 437 | GGCGAAGAGCCCTCCAAACTGAGGCTG |
| Pro Insert at 275/276 | 466 | GAGCCCTCCTTTGATGGGGCGAAACTGAGGCTG |
| I276P | 439 | GAGCCCTCCTTTGGGGCGAAACTGAGG |
| I276P, K277A | 468 | GAAGAGCCCTCCGGCGGGGCGAAACTGAGG |
| I276D | 469 | CCCTCCTTTATCGCGAAACTGAGG |
| I276H | 470 | CCCTCCTTTGTGGCGAAACTGAGG |
| I276Y | 471 | CCCTCCTTTATAGCGAAACTGAGG |
| I276A | 472 | CCCTCCTTTGGCGCGAAACTGAGG |
| I276W | 473 | CCCTCCTTTCCAGCGAAACTGAGG |
| I276S | 474 | CCCTCCTTTAGAGCGAAACTGAGG |
| F274L, R275H, I276S, K277T | 449 | GGCGAAGAGCCCTCCGGTAGAGTGTAACTGAGG CTGGCTGTAA |

*Notation: Letter to left of amino acid position numberal is natural amino acid at that position and letter to right is the variant amino acid. See FIGS. 20 and 21.

3. Bacterial Transformation and DNA Preparation

The mutant t-PA constructs generated using the protocol above were transformed into E. coli host strain MM294tonA using the standard $CaCl_2$ procedure (Maniatis et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis (Kleckner et al., J. Mol. Biol., 116:125–159 (1977)), into E. coli host MM294 (ATCC 31,446).

Individual colonies of bacterial transformants were selected and grown to saturation in 35 ml LB broth containing 150 µg/ml carbenicillin. DNA was extracted and purified using a kit purchased from Qiagen Inc. (catalog number 41021). The plasmids were analyzed by sequencing and by restriction endonuclease digestion and agarose gel electrophoresis.

4. Transfection of Human Embryonic Kidney 293 Cells 293 cells were grown to 70% confluence in 6-well plates. 2.5 µg of t-PA plasmid DNA mutant was dissolved in 150 µl of 1 mM Tris-HCl, 0.1 mM EDTA, 0.227M $CaCl_2$. Added to this (dropwise while vortexing) was 150 µl of 50 mM HEPES buffer (pH 7.35), 280 mM NaCl, 1.5 mM $NaPO_4$, and the precipitate was allowed to form for ten min. at 25° C. The suspended precipitate was then added to the cells in the individual wells in a 6-well plate and allowed to settle for four hours in the incubator. The medium was then aspirated off and 1 ml of 20% glycerol in PBS was added for 30 sec. The cells were washed twice, first with 3 ml, then with 1 ml, of serum-free medium. Then 3 ml of fresh medium was added and the cells were incubated for five days. The medium was then collected and assayed.

When single-chain t-PA was required, the procedure was as described above except that plasminogen depleted serum was used during the growth phase of the cells.

Biological Assays

A. t-Pa Quantitation

The amount of t-PA present in the cell culture supernatants was determined by the ELISA procedure using polyclonal antibodies prepared against wild-type t-PA.

B. S-2251 Assay (Plasminogen Activator Assay)

This assay is an indirect assay for t-PA activity. In this assay, plasminogen is converted to plasmin by the action of t-PA, and plasmin cleaves the S-2251 substrate to release the paranitroanilide chromophore. Production of this chromophore is then measured over time. The protocols for the fibrin-stimulated, fibrinogen stimulated, and unstimulated assay have been detailed previously (Bennett et al. JBC 266, pp 5191–5201, (1991)). For this study, all samples were incubated with sepharose-plasmin prior to assay. Samples susceptible to cleavage by plasmin were converted to the two-chain during this step.

The variants prepared using the oligonucleotides set forth above (Oligo numbers 437, 439 and 466 to 474), when tested for activity according to the S-2251 assay, gave the results set forth in FIG. 17. From this data it can be seen that in the presence of fibrin all of the variants exhibited plasminogen activator activity which was equal to or greater than that of wild-type t-PA. In contrast, these variants had lower than wild-type activity in the presence of fibrinogen, or in the absence of a stimulator. These results indicate that the variants are more fibrin specific than wild-type t-PA.

The fold increase in fibrin specificity for these variants over that of wild-type tPA was determined by taking the ratio of the relative activities of the variants in the presence of fibrin to that in the presence of fibrinogen. The results are shown in Table III below. In our hands, the plasminogen activator activity of wild-type t-PA in the S2251 assay is approximately six-fold greater when fibrin is used compared to fibrinogen (Bennett et al., JBC 266, pp 5191–5201, 1991)). The values for the variants are in excess to that difference.

TABLE III

| Mutant | Activity Ratio (Fibrin/Fibrinogen) |
| --- | --- |
| Des 275–277 | 12.3 |
| I276P, K277A | 6.5 |
| I276P, K277I | 7.5 |
| I276P | 9.7 |
| Pro insert at 275/276 | 2.4 |
| I276D | 6.0 |
| I276S | 19.7 |
| I276A | 5.4 |
| I276H | 16.5 |
| I276W | 7.1 |
| I276Y | 7.6 |

CONCLUSION

The above results demonstrate that mutation at residue 275 of t-PA may be more efficacious than the natural form for two separate reasons:

1. Increased specificity: Assays of t-PA function indicate a more active/specific protein.

2. Decreased in vivo plasma inhibitor binding: in vivo inhibition of such mutants indicate a decrease in inactivation by certain protease inhibitors. This should allow for the circulation of the active uncomplexed form of t-PA thereby allowing for increased functional t-PA to dissolve a clot.

The scientific literature is contradictory on the enzymatic properties of the one-chain form of t-PA. In order to better understand the function of t-PA one can look to homologous proteins. Extensive investigations have been performed in the serine proteases trypsin and chymotrypsin. The t-PA protease domain is very similar to these proteins and is expected to function in a similar manner. Based on the mechanism of function determined for trypsin and chymotrypsin, preventing cleavage at arginine 275 of t-PA would be expected to affect only the functional characteristics of the protease domain. The increased fibrin affinity of the mutants is therefore surprising.

Regardless of the mechanism(s) involved (increased specificity, lack of protease inhibitor binding, increased affinity for fibrin, or combination of these), when one mutant was tested for its ability to lyse a blocked vein in vivo, it was found to be approximately 2.5 times more active than the t-PA of natural sequence. As discussed previously, the one-chain form of t-PA has been shown to be converted to the two-chain form at the site of a clot. Such a conversion would destroy any advantage associated with the one-chain form. Only a mutated form of t-PA is capable of being converted to the two-chain form by physiologic proteases will be able to preserve its advantages once at the site of a clot. In addition, although consequent clot lysis activity was not apparently increased, pharmacokinetic data indicates that at equivalent dose rates, the EIK mutant gives plasma concentrations that are 1.7 fold higher in rabbits and 2.2 fold higher in monkeys than wild-type (RIK) t-PA.

The data shown above (Example 2) indicate that the variants set forth above (Oligo numbers 437, 439 and 466–474) show strikingly higher fibrin specificity than wild-type t-PA.

Having described the preferred embodiment of the present invention, it will appear to those ordinarily skilled in the art that various modifications may be made to the disclosed embodiment, and that such modifications are intended to be within the scope of the present invention.

What is claimed is:

1. A DNA molecule which is a recombinant DNA molecule or a cDNA molecule encoding a human tissue plasminogen activator (t-PA) comprising:
   a) an amino acid other than arginine at a position corresponding to position 275 of the amino acid sequence of wild-type t-PA; and
   b) an amino acid other than lysine at a position corresponding to position 277 of the amino acid sequence of wild-type t-PA; and
   c) an amino acid other than isoleucine at a position corresponding to position 276 of the amino acid sequence of wild-type t-PA.

2. A DNA molecule which is a recombinant DNA molecule or a cDNA molecule encoding a human tissue plasminogen activator (t-PA) comprising:
   a) an amino acid other than arginine at a position corresponding to position 275 of the amino acid sequence of wild-type t-PA; and
   b) an amino acid other than isoleucine at a position corresponding to position 276 of the amino acid sequence of wild-type t-PA.

3. A DNA molecule which is a recombinant DNA molecule or a cDNA molecule encoding a human tissue plasminogen activator (t-PA) comprising:
   a) an amino acid other than lysine at a position corresponding to position 277 of the amino acid sequence of wild-type t-PA; and
   c) an amino acid other than isoleucine at a position corresponding to position 276 of the amino acid sequence of wild-type t-PA.

4. An expression vector capable of expressing the DNA according to claim 1, 2 or 3.

5. A cell culture transfected with the vector according to claim 4.

6. A method of using the DNA according to claim 1, 2 or 3 to produce a human tissue plasminogen activator as an expression product.

7. A DNA molecule according to claim 1, 2 or 3 wherein the isoleucine at position 276 of the amino acid sequence of wild-type t-PA is replaced with a proline.

* * * * *

UNITED STATES PATENT AND TRADEMARK OFFICE
CERTIFICATE OF CORRECTION

PATENT NO. : 5,714,372

DATED : February 3, 1998

INVENTOR(S) : VEHAR et al.

It is certified that error appears in the above-identified patent and that said Letters Patent is hereby corrected as shown below:

Column 3, line 30, delete "P276I1277" and insert therefor --P276I277--.

Column 3, line 30, delete "E275P276I1277" and insert therefor --E275P276I277--.

Column 5, line 25, immediately preceding "kringle" insert --3)--.

Column 11, line 1, delete "Saccharomyces" and insert therefor --*Saccharomyces*--.

Column 17, line 8, delete "270" and insert therefor --275--.

Column 19, line 50, delete "pPA183'ΔX 10" and insert therefor --pPA183'ΔX10--.

Column 20, line 61, delete the space immediately preceding "U.S.".

Column 22, line 25, immediately following "(-HGT)" insert --)--.

Column 23, line 5, delete "pF18CIS" and insert therefor --pF8CIS--.

Column 24, line 32, delete "amp'" and insert therefor --$amp^r$--.

Column 24, line 48, beneath "AAC (asn) N", insert --CCC (pro) P--.

Column 24, line 50, beneath "CAC (his) H", insert --ATC (ile) I--.

UNITED STATES PATENT AND TRADEMARK OFFICE
CERTIFICATE OF CORRECTION

PATENT NO. : 5,714,372

DATED : February 3, 1998

INVENTOR(S) : VEHAR et al.

It is certified that error appears in the above-indentified patent and that said Letters Patent is hereby corrected as shown below:

Column 25, line 8, immediately following "(1983)" insert --)--.

Column 25, line 29, immediately following "(1983)" insert --)--.

Column 26, line 55, immediately preceding "standard" delete "s" and insert therefor --a--.

Column 29, line 43, delete "benamidine" and insert therefor --benzamidine--.

Column 30, line 64, immediately following "(1982)" insert --)--.

Column 32, in the table, immediately below line 37 which begins "I266P 439" insert:
--I276P,     467     GAAGAGCCCTCCAATGGGGCGAAACTGAGG
K277I--.

Claim 1, column 35, line 8, delete "ammo" and insert therefor --amino--.

Signed and Sealed this

Third Day of November, 1998

Attest:

BRUCE LEHMAN

*Attesting Officer*     Commissioner of Patents and Trademarks